US010400288B2

(12) United States Patent
Rønfeldt Thomsen et al.

(10) Patent No.: US 10,400,288 B2
(45) Date of Patent: Sep. 3, 2019

(54) MICRORNA-BASED METHOD FOR EARLY DETECTION OF PROSTATE CANCER IN URINE SAMPLES

(71) Applicants: Exiqon A/S, Vedbaek (DK); Aarhus Universitet, Århus C (DK); Region Midtjylland, Viborg (DK)

(72) Inventors: Anni Rønfeldt Thomsen, Virum (DK); Jacob Christian Fredsøe, Risskov (DK); Karina Dalsgaard Sørensen, Århus C (DK); Lars Kongsbak, Holte (DK); Peter Mouritzen, Jyllinge (DK); Torben Ørntoft, Silkeborg (DK)

(73) Assignees: Aarhus Universitet, Århus C (DK); Region Midtjylland, Viborg (DK); QIAGEN GmbH, Hilden (DE)

( * ) Notice: Subject to any disclaimer, the term of this patent is extended or adjusted under 35 U.S.C. 154(b) by 0 days.

(21) Appl. No.: 15/550,416

(22) PCT Filed: Feb. 5, 2016

(86) PCT No.: PCT/DK2016/050032
§ 371 (c)(1),
(2) Date: Aug. 11, 2017

(87) PCT Pub. No.: WO2016/127998
PCT Pub. Date: Aug. 18, 2016

(65) Prior Publication Data
US 2018/0030542 A1    Feb. 1, 2018

(30) Foreign Application Priority Data

Feb. 11, 2015   (DK) .................................. 2015 00079
Dec. 21, 2015   (DK) .................................. 2015 00825

(51) Int. Cl.
*C12Q 1/6886* (2018.01)
*G16B 25/00* (2019.01)

(52) U.S. Cl.
CPC ........... *C12Q 1/6886* (2013.01); *G16B 25/00* (2019.02); *C12Q 2600/106* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2014/0235469 | A1  | 8/2014  | Shelton et al. |
| 2014/0309130 | A1  | 10/2014 | Haj-Ahmad |
| 2018/0002762 | A1* | 1/2018  | Chakravarti ......... C12Q 1/6886 |
| 2018/0044737 | A1  | 2/2018  | Ronfeldt Thomsen et al. |

FOREIGN PATENT DOCUMENTS

| CN | 103882118 A | 6/2014 |
| EP | 2341145 A1 | 7/2011 |
| WO | WO-2009/036236 A1 | 3/2009 |

(Continued)

OTHER PUBLICATIONS

"Arraystar Handbook miRStar(TM) PCR Array Systems," Jul. 3, 2014, http://web.archive.org/web/20150213151200/http://www.arraystar.com/Manage/UploadFile/Handbook/Arraystar%20Handbook-miRStar%20PCR%20Array%20Systems.pdf, retrieved Feb. 13, 2015 (36 pages).
International Search Report for International Patent Application No. PCT/DK2016/050032, dated May 25, 2016 (5 pages).
Mlcochova et al., "Urine microRNAs as potential noninvasive biomarkers in urologic cancers," Urol Oncol. 32(1):41.e1-9 (2014).
Search Report for Danish Patent Application No. DK PA 2015 00079, dated Sep. 11, 2015 (9 pages).
Fu et al., "Deregulated microRNAs in CD4 + T Cells from individuals with latent tuberculosis versus active tuberculosis," J. Cell. Mol. Med. 18(3): 503-513 (2014).

(Continued)

*Primary Examiner* — Sean McGarry
(74) *Attorney, Agent, or Firm* — Clark & Elbing LLP

(57) ABSTRACT

The present application concerns a new in vitro method for assessing the risk that a subject suffers from prostate cancer. The method comprises measuring the expression level the level of at least two miRs selected from group of miRs consisting of: hsa-let-7a-5p, hsa-let-7b-5p, hsa-let-7c-5p, hsa-let-7e-5p, hsa-let-7f-5p, hsa-let-7g-5p, hsa-miR-100-5p, hsa-miR-106a-5p, hsa-miR-10a-5p, hsa-miR-10b-5p, hsa-miR-1238-3p, hsa-miR-125b-5p, hsa-miR-1260a, hsa-miR-130a-3p, hsa-miR-132-3p, hsa-miR-135a-5p, hsa-miR-135b-5p, hsa-miR-136-5p, hsa-miR-140-3p, hsa-miR-141-3p, hsa-miR-142-3p, hsa-miR-146a-5p, hsa-miR-148a-3p, hsa-miR-151a-3p, hsa-miR-151a-5p, hsa-miR-15b-5p, hsa-miR-16-5p, hsa-miR-191-5p, hsa-miR-1972, hsa-miR-19a-3p, hsa-miR-19b-3p, hsa-miR-200a-3p, hsa-miR-200b-3p, hsa-miR-200b-5p, hsa-miR-200c-3p, hsa-miR-203a, hsa-miR-204-5p, hsa-miR-205-5p, hsa-miR-20a-5p, hsa-miR-210, hsa-miR-222-3p, hsa-miR-223-3p, hsa-miR-22-5p, hsa-miR-23a-3p, hsa-miR-23b-3p, hsa-miR-24-3p, hsa-miR-25-3p, hsa-miR-26a-5p, hsa-miR-27b-3p, hsa-miR-29a-3p, hsa-miR-29b-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-320b, hsa-miR-320c, hsa-miR-331-3p, hsa-miR-362-3p, hsa-miR-362-5p, hsa-miR-363-3p, hsa-miR-375, hsa-miR-378a-3p, hsa-miR-425-3p, hsa-miR-425-5p, hsa-miR-455-3p, hsa-miR-490-3p, hsa-miR-660-5p, hsa-miR-93-5p, hsa-miR-99a-5p, and hsa-miR-99b-5p, in a urine sample from the patient. A method wherein the at least two selected miRs are: hsa-miR-30c-5p, hsa-miR-222-3p, and hsa-miR-24-3p is preferred. The application also concerns a kit of parts to perform the in vitro method.

34 Claims, 14 Drawing Sheets

(56) References Cited

FOREIGN PATENT DOCUMENTS

Figure 2:
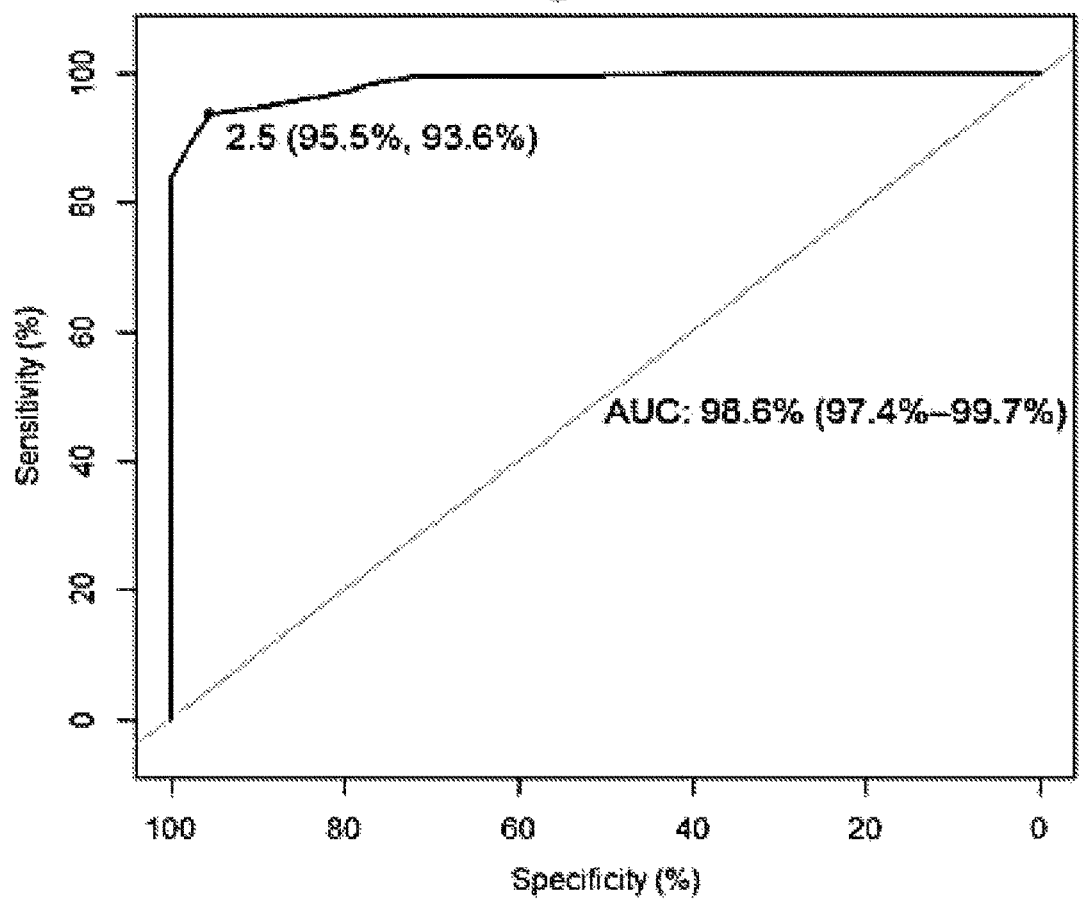

| WO | WO-2011/057003 A2 | 5/2011 |
| --- | --- | --- |
| WO | WO-2011/127219 A1 | 10/2011 |
| WO | WO-2012015765 A2 | 2/2012 |
| WO | WO-2013/063544 A1 | 5/2013 |
| WO | WO-2014/071205 A1 | 5/2014 |
| WO | WO-2014/085906 A1 | 6/2014 |
| WO | WO-2016/046365 A1 | 3/2016 |

OTHER PUBLICATIONS

Kim et al., "Virus-Encoded microRNAs HSV1-MIR-H18 and HSV2-MIR-H9-5p: Valuable Diagnostic Biomarkers for Prostate Cancer," Urology 84(4): S71, MP-12.03, 2014 (1 page).

Song et al., "Expression Profile Analysis of microRNAs in Prostate Cancer by Next-Generation Sequencing," The Prostate 75(5): 500-516 (2015).

\* cited by examiner

Fig. 1
A 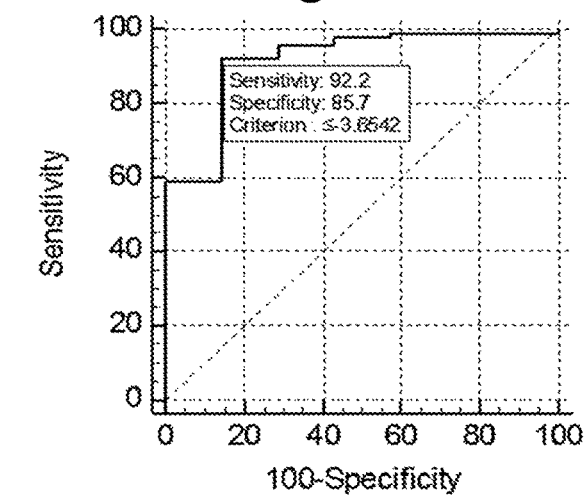
B 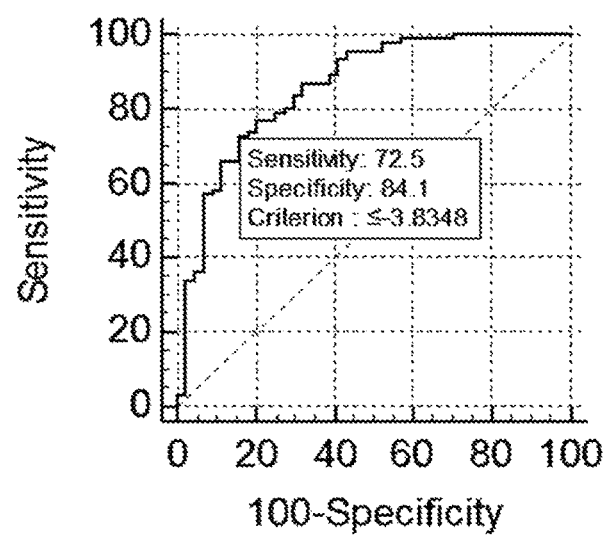
C 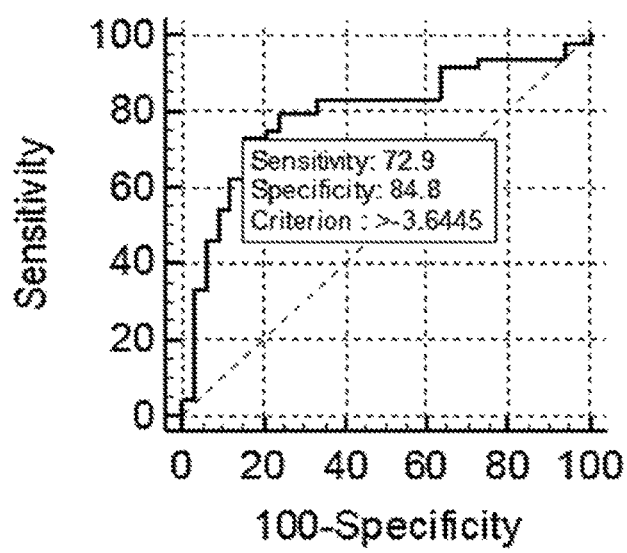

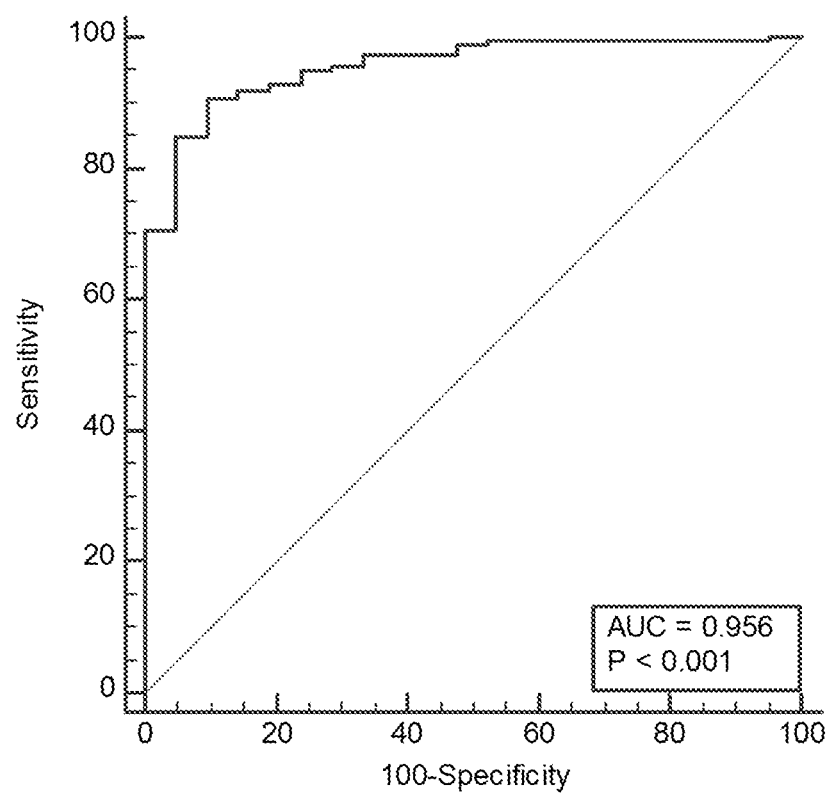

Ratio based 3miR_1 classifiers - Validation cohort

Ratio based 3miR_2 classifiers - Validation cohort (PSA < 10ng/mL )

MICRORNA-BASED METHOD FOR EARLY DETECTION OF PROSTATE CANCER IN URINE SAMPLES

FIELD OF THE INVENTION

The present invention relates to a method for reducing the problem of over-diagnosis in prostate cancer. By measuring the level of a few characteristic microRNA biomarkers in urine, the method can preselect individuals with prostate cancer that should benefit from further invasive diagnostic procedures.

BACKGROUND OF THE INVENTION

Prostate cancer (PC) is a malignant tumor that originates in the prostate gland it is the most commonly diagnosed and treated malignancy and is one of the leading causes of cancer-related death among males in western countries (1). About 1 in 6 men will be diagnosed with prostate cancer over the course of their life and most elderly men eventually develop the disease.

At the time of diagnosis, most men have localized prostate cancer (cancer confined to the prostate gland) with excellent prognosis. About 5% of men are diagnosed with advanced or distant cancer that has spread throughout the body. For these men, the 5-year relative survival rate is only 29%. Early detection of PC is however crucial since curative treatment only is possible for non-metastatic PC.

PC is typically diagnosed on the basis of increased serum prostate specific antigen (PSA) levels followed by histopathological inspection of needle biopsies. The use of PSA for PC detection, however, is associated with considerable false positive rates. Using a PSA cutoff of 4.0 ng/ml for screening, there is a 65% false-positive and a 20% false-negative rate (2). In particular, PSA levels in the intermediate range area (2-10 ng/mL) presents a gray zone area with very low predictive value. Naturally, such rates have spurred a search for other biomarkers, in particular biomarkers that are found in easy accessible bio-fluids and which are relatively cheap to assess. Until now, we are not aware that this endeavor has been successful.

Hence, there is a serious and unmet need to develop methods which can improve the early diagnosis of PC and reduce the number of men referred to needless biopsies. The present study presents one such method.

An emerging new class of potential biomarkers for prostate cancer is the microRNAs (miRs).

MicroRNAs comprise a class of endogenous small non-coding regulatory RNAs (~22 nt), which control gene expression at the posttranscriptional level in diverse organisms, including mammals (3). MicroRNAs are transcribed as long imperfect paired stem-loop primary microRNA transcripts (pri-microRNAs) by RNA polymerase II, and further processed into hairpin precursor microRNAs (pre-microRNAs) by the nuclear RNase III endonuclease, Drosha (4). After export to the cytoplasm by Exportin-5-Ran-GTP, another RNase III endonuclease, Dicer, cleaves the pre-microRNA into a mature ~22 nt microRNA duplex (4). Mature microRNAs mediate their function while incorporated in the microRNA-induced silencing complex (miRISC). The microRNA guides this complex to perfect/near perfect complementary target mRNAs, leading to either translational inhibition or mRNA degradation (5).

MicroRNAs are one of the most abundant classes of gene regulatory molecules and the latest release of the miRBase (version 21) contains 2588 mature human microRNAs (1881 precursors) http://www.mirbase.org/ (6). Together microRNAs have been estimated to regulate up to two thirds of all human mRNAs. Consequently, microRNAs influence numerous processes in the cell, for instance cell differentiation, cell cycle progression and apoptosis, and deregulation of microRNAs are often connected to human pathologies, including cancer (7). Additionally, some microRNAs appear to be cell type and disease specific and deregulated microRNA expression has been associated with both development and progression of cancer (8). Thus, aberrant microRNA expression has been investigated as a promising potential source of novel biomarkers for early cancer diagnosis (8). Moreover, microRNAs have potential to be used as targets of microRNA-based therapeutics for cancer (9). Several microRNA profiling studies have also reported aberrantly expressed microRNAs in the development and/or progression of PC (10). However, most of the microRNA biomarker studies in PC published to date have used relatively low patient sample numbers and often lack stringent independent clinical validation to confirm the biomarker potential of the identified microRNA candidates.

Importantly, to the best of our knowledge, no diagnostic method based on microRNA biomarkers detected in non-invasive samples such as urine has emerged.

Here we performed miRnome profiling of more than 750 of the most abundant microRNAs and selected the 183 microRNAs detectable in cell free urine across different disease stages (Example 1). From these 183 microRNAs we identified significantly aberrant regulated microRNAs in patients with benign prostate hyperplasia vs. PC patients where urine was collected prior to prostate removal by radical prostatectomy (RP) (Example 2). From this dataset we have identified a small group of miRs which are significantly different expressed in PC relative to non-PC subjects. We furthermore identified a diagnostic classifier consisting of only 2 microRNAs in cohort 1 and evaluated its diagnostic accuracy. This 2 microRNA classifier was successfully validated in an independent cohort 2 (Example 3). To investigate the robustness we applied the assay to yet an independent cohort (cohort 3) where specimens were sampled and processed with a considerably different methodology than cohort 1 and 2 (Example 4). Interestingly, the 2 microRNA classifier was also successfully validated in this cohort.

Further, as the discovery cohort suffered from being limited in the number of controls it appeared advantageous to merge cohort 1 and cohort 2 in order to build a classifier with a stronger statistic power based on the merged data. This approach was pursued in Example 5, and resulted in identification of a slightly different 20-miR classifier, but with a surprisingly high AUC of 0.99 with a specificity of 95.5% and a sensitivity of 93.6%.

The 2 miR diagnostic classifier (involving a ratio calculation) demonstrated improved accuracy compared to all single miRNAs tested. Interestingly, all the identified classifiers appeared to have an significantly improved accuracy compared with the total prostate specific antigen (tPSA) test. AUC of this test has been reported to be as low as 0.59, (11) or even lower (12).

To confirm the validity of the identified microRNA biomarkers we included an additional set of 205 PC samples and repeated the classifier building and validation in two new cohorts (cohort 4 and cohort 5, respectively), where the non-cancer samples from cohort 1 and 2 were distributed evenly and randomly between the two cohorts. Also, a different statistical method for assay selection and classifier building was applied, along with more stringent data filtering parameters.

From this study we identified diagnostic classifiers consisting of 3 to 10 microRNAs (with a significant overlap with the previous studies) and evaluated their diagnostic potential in cohort 4 (Example 8). The classifiers were successfully validated in an independent validation cohort 5 (example 9). Surprisingly, the classifiers were even more successful when validated in the intended use sub-population; patients with PSA levels below 10 ng/mL (Example 10).

As mentioned, ratio based classifiers are attractive due to their ability to circumvent the need for normalization assays, thereby reducing the number of assays included in the test. We identified two such ratio based classifiers consisting each of only three assays with high diagnostic potential in the discovery cohort 4 (example 11). The two ratio based classifiers were successfully validated in the validation cohort 5 (example 12). Finally, these ratio based classifiers were validated in the intended use sub population, where they proved to be even more accurate. Again, both the 3-10miR classifiers and the two ratio based classifiers demonstrated improved accuracy compared to all single miRNAs tested. Interestingly, all the identified classifiers appeared to have a significantly improved accuracy compared with the total prostate specific antigen (tPSA) test. As was the case for the 2 miR classifier of example 4, we also tested the diagnostic robustness of the two 3-miR ratio-based classifiers in the fundamentally different cohort 3. This analysis show that at least one of the 3-miR ratio-based classifiers is robust and validate even in cohort 3.

SUMMARY OF THE INVENTION

As the prostate specific antigen (PSA) method is associated with considerable false negative rates and does not distinguish well between clinically indolent or aggressive tumors, there is a need for novel markers of prostate cancer that can be used on their own or in combination with existing markers. The present invention present one set of markers and a method to apply them for preselection patients for PC diagnosis.

In first aspect, the invention thus concerns an in vitro method for assessing the risk that a subject suffers from prostate cancer, comprising measuring the expression level of at least two miRs selected from group of miRs consisting of: hsa-let-7a-5p, hsa-let-7b-5p, hsa-let-7c-5p, hsa-let-7e-5p, hsa-let-7f-5p, hsa-let-7g-5p, hsa-miR-100-5p, hsa-miR-106a-5p, hsa-miR-10a-5p, hsa-miR-10b-5p, hsa-miR-1238-3p, hsa-miR-125b-5p, hsa-miR-1260a, hsa-miR-130a-3p, hsa-miR-132-3p, hsa-miR-135a-5p, hsa-miR-135b-5p, hsa-miR-136-5p, hsa-miR-140-3p, hsa-miR-141-3p, hsa-miR-142-3p, hsa-miR-146a-5p, hsa-miR-148a-3p, hsa-miR-151a-3p, hsa-miR-151a-5p, hsa-miR-15b-5p, hsa-miR-16-5p, hsa-miR-191-5p, hsa-miR-1972, hsa-miR-19a-3p, hsa-miR-19b-3p, hsa-miR-200a-3p, hsa-miR-200b-3p, hsa-miR-200b-5p, hsa-miR-200c-3p, hsa-miR-203a, hsa-miR-204-5p, hsa-miR-205-5p, hsa-miR-20a-5p, hsa-miR-210, hsa-miR-222-3p, hsa-miR-223-3p, hsa-miR-22-5p, hsa-miR-23a-3p, hsa-miR-23b-3p, hsa-miR-24-3p, hsa-miR-25-3p, hsa-miR-26a-5p, hsa-miR-27b-3p, hsa-miR-29a-3p, hsa-miR-29b-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-320b, hsa-miR-320c, hsa-miR-331-3p, hsa-miR-362-3p, hsa-miR-362-5p, hsa-miR-363-3p, hsa-miR-375, hsa-miR-378a-3p, hsa-miR-425-3p, hsa-miR-425-5p, hsa-miR-455-3p, hsa-miR-490-3p, hsa-miR-660-5p, hsa-miR-93-5p, hsa-miR-99a-5p, and hsa-miR-99b-5p, in a urine sample from said subject, wherein a changed expression level of said at least 2 miRs, as compared to healthy donors, indicates an increased probability of said subject suffering from prostate cancer.

The most preferred embodiment of the invention is the in vitro method, wherein the at least two selected miRs are hsa-miR-24-3p, hsa-miR-222-3p, and hsa-miR-30c-5p. An almost equally preferred embodiment is the in vitro method, wherein the at least two selected miRs are hsa-miR-24-3p, hsa-miR-222-3p, and hsa-miR-30a-5p.

It is an important aspect of the invention to apply the method to a population of patients wherein a previous standard prostate specific antigen (PSA) measurement has indicated that their serum PSA level is below 10 ng/mL.

An vitro diagnostic method which comprise calculating the diagnostic score (S) is an useful aspect of the invention.

Yet an aspect the invention relates to a kit for in vitro assessment of the risk that a subject suffers from prostate cancer, comprising aliquots of the reagents needed for measuring the expression level the level of at least two miRs selected from group of miRs consisting of: hsa-let-7a-5p, hsa-let-7b-5p, hsa-let-7c-5p, hsa-let-7e-5p, hsa-let-7f-5p, hsa-let-7g-5p, hsa-miR-100-5p, hsa-miR-106a-5p, hsa-miR-10a-5p, hsa-miR-10b-5p, hsa-miR-1238-3p, hsa-miR-125b-5p, hsa-miR-1260a, hsa-miR-130a-3p, hsa-miR-132-3p, hsa-miR-135a-5p, hsa-miR-135b-5p, hsa-miR-136-5p, hsa-miR-140-3p, hsa-miR-141-3p, hsa-miR-142-3p, hsa-miR-146a-5p, hsa-miR-148a-3p, hsa-miR-151a-3p, hsa-miR-151a-5p, hsa-miR-15b-5p, hsa-miR-16-5p, hsa-miR-191-5p, hsa-miR-1972, hsa-miR-19a-3p, hsa-miR-19b-3p, hsa-miR-200a-3p, hsa-miR-200b-3p, hsa-miR-200b-5p, hsa-miR-200c-3p, hsa-miR-203a, hsa-miR-204-5p, hsa-miR-205-5p, hsa-miR-20a-5p, hsa-miR-210, hsa-miR-222-3p, hsa-miR-223-3p, hsa-miR-22-5p, hsa-miR-23a-3p, hsa-miR-23b-3p, hsa-miR-24-3p, hsa-miR-25-3p, hsa-miR-26a-5p, hsa-miR-27b-3p, hsa-miR-29a-3p, hsa-miR-29b-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-320b, hsa-miR-320c, hsa-miR-331-3p, hsa-miR-362-3p, hsa-miR-362-5p, hsa-miR-363-3p, hsa-miR-375, hsa-miR-378a-3p, hsa-miR-425-3p, hsa-miR-425-5p, hsa-miR-455-3p, hsa-miR-490-3p, hsa-miR-660-5p, hsa-miR-93-5p, hsa-miR-99a-5p, and hsa-miR-99b-5p, in a urine sample from said subject, wherein a changed expression level of said at least 2 miRs, as compared to healthy donors, indicates an increased probability of said subject suffering from prostate cancer.

Definitions

The Expression "microRNA", "miRNA" and "miR" are Used Synonymously to Refer to an about 18-25 nucleotide (nt) long, non-coding RNAs derived from endogenous genes. MicroRNAs are processed from longer (ca 75 nt) hairpin-like precursors termed pre-miRs. MicroRNAs assemble in complexes termed miRNPs and recognize their targets by antisense complementarity. If the microRNAs match 100% their target, i.e. the complementarity is complete, the target mRNA is cleaved, and the miR acts like a siRNA. If the match is incomplete, i.e. the complementarity is partial, then the translation of the target mRNA is blocked. In general the naming of mirRs refer to the nomenclature of miRBase (version 21), see table 11.

The term "expression", as used herein, refers to the transcription and/or accumulation of RNA-molecules within a cell or in a cell-free biofluid.

The terms "Q-PCR" or "q-PCR" refers to quantitative polymerase chain reaction. Q-PCR is highly sensitive method for quantifying the amounts of specific DNA (and RNA) species in a test sample. As quantification of RNA by the PCR technique requires that the RNA is reverse transcribed it is often referred to as "qRT-PCR" or "RT-Q-PCR" to indicate that quantitative PCR is used to quantify specific RNAs. A thorough treatise of the Q-PCR and qRT-PCR techniques can be found in (13). In the present context "Q-PCR", "q-PCR", "qRT-PCR", "QRT-PCR" or "RT-Q-PCR" can be used synonymously as a method of quantifying the amounts of specific RNA (or DNA) species.

In the present context the terms "expression level of a miR", "miR expression level" and "level of a miR" are used synonymously as a measure of the "amount of a specific miR" that is detected in the sample. The "amount of a specific miR" may be expressed in either absolute, relative or normalised measures and refers to values obtained by both quantitative, as well as qualitative methods. One particularly preferred measure of the "amount of a specific miR" is the Crossing point (Cp) value obtained by real-time RT-Q-PCR (qRT-PCR) as described below and in the examples, but "amount" may as well be quantified by digital PCR, or various Next Generation Sequencing methods. In certain situations, e.g. when ratios of miR expression levels are used to calculate a diagnostic score the absolute determined expression levels of the miRs suffice. However, as an alternative to making determinations based on the absolute expression level of the miRs, determinations may be based on the normalised expression levels of the miRs.

Expression levels are normalised by correcting the absolute expression level of a miR by comparing its expression to the expression of a gene that is constitutively or nearly constitutively expressed. Suitable genes often used for normalisation include housekeeping genes such as the actin gene. In the present study we use a collection miRs for normalizing. Typically a collection of 3 or 5 miRNAs can are used to calculate a mean normalization value. The preferred 3 miR-normalizer is: hsa-miR-200b-3p, hsa-miR-27b-3p, and hsa-miR-30b-5p (see example 8). The preferred 5 miR-normalizer is: hsa-miR-20a-5p, hsa-miR-30b-5p, hsa-let-7a-5p, hsa-miR-27b-3p, and hsa-miR-23b-3p (see example 5).

"ROC-curve" is short for receiver operating characteristic curve. (ROC) curves are widely used to compare diagnostic tests.

The expressions "healthy individual", "healthy donor" and "healthy control" are used synonymously to refer to apparently healthy individuals with no overt indication of prostate cancer in contrast to differentiate them from prostate cancer patients.

Specimens

Samples were collected at Department of Urology, Aarhus University Hospital, Denmark (from 1997-2005) or by Department of Oncology, The Medical School, Sheffield, UK.

The term "robustness" in connection with miR classifier is used herein to describe a classifier which provide relative similar outcome with respect to differentiating between PC and non-PC patients even though somewhat different sampling and quantitation methodologies are used.

"UniRT" is a Q-PCR method marketed by Exiqon A/S. The method and its performance is described in Example 1 and 7 and in Danish Patent Application PA 2009 00156, EP2391736 and Mestdagh et al. Nat Methods. 2014 August; 11(8):809-15, In the present context the "cut-off value" is a threshold-value above (or below) which a value, calculated to represent the level of a number of miRs indicate that a test cell sample is from a colon cancer.

Embodiments of the present invention are described below, by way of examples only.

DETAILED DISCLOSURE OF THE INVENTION

The technical problem underlying the invention is the provision of an improved in vitro method for assessing the risk that a subject suffers from prostate cancer. In particularly a method which relayed on non-invasive procedures and consequently useful for screening purposes was sought in the hope that it could supplement the widespread PSA test.

Both in the discovery cohort (see example 2) in the validation cohort (example 3) and in the alternative analysis presented in examples 5 and 8, we have consistently observed that the expression level of a group of miRs in a urine sample from a patient can be used as a diagnostic classifier of prostate cancer (PC). Collectively the group of miRs consist of 76 miRs, see table 1.

TABLE 1

| All miRs | A | B | C | D | E | F | G | H |
|---|---|---|---|---|---|---|---|---|
| hsa-let-7a-5p | X | X | X | X |   |   | X | X |
| hsa-let-7b-5p |   |   |   |   |   | X |   | X |
| hsa-let-7c-5p |   |   |   |   |   | X |   |   |
| hsa-let-7e-5p | X | X | X | X |   |   |   |   |
| hsa-let-7f-5p |   |   |   |   |   |   | X | X |
| hsa-let-7g-5p |   |   |   |   |   |   | X | X |
| hsa-miR-100-5p |   |   |   |   |   | X |   |   |
| hsa-miR-106a-5p |   |   |   |   |   | X |   |   |
| hsa-miR-10a-5p |   |   |   |   |   | X |   |   |
| hsa-miR-10b-5p | X | X | X | X |   | X |   | X |
| hsa-miR-1238-3p | X | X | X | X |   |   |   |   |
| hsa-miR-125b-5p |   |   |   |   |   | X |   | X |
| hsa-miR-1260a |   |   |   |   |   |   | X | X |
| hsa-miR-130a-3p | X | X | X | X |   | X |   |   |
| hsa-miR-132-3p |   |   |   |   |   | X |   |   |
| hsa-miR-135a-5p |   |   |   |   |   | X |   |   |
| hsa-miR-135b-5p | X | X | X | X |   | X |   |   |
| hsa-miR-136-5p | X | X | X | X |   |   |   |   |
| hsa-miR-140-3p | X | X | X | X |   | X |   |   |
| hsa-miR-141-3p | X | X | X | X | X | X |   | X |
| hsa-miR-142-3p | X | X | X | X |   | X |   |   |
| hsa-miR-146a-5p | X | X | X | X |   | X |   |   |
| hsa-miR-148a-3p |   |   |   |   |   | X |   |   |
| hsa-miR-151a-3p | X | X | X | X |   | X |   |   |
| hsa-miR-151a-5p |   |   |   |   |   | X |   |   |
| hsa-miR-15b-5p |   |   |   |   |   | X |   |   |
| hsa-miR-16-5p | X | X | X | X | X | X |   | X |
| hsa-miR-191-5p | X | X | X | X |   | X |   |   |
| hsa-miR-1972 |   |   |   |   |   | X |   |   |
| hsa-miR-19a-3p | X | X | X | X |   |   |   |   |
| hsa-miR-19b-3p |   |   |   |   |   |   | X | X |
| hsa-miR-200a-3p |   |   |   |   |   | X |   |   |
| hsa-miR-200b-3p | X | X | X | X |   | X | X | X |
| hsa-miR-200b-5p |   |   |   |   |   | X |   |   |
| hsa-miR-200c-3p | X | X | X | X |   | X |   | X |
| hsa-miR-203a | X | X | X | X |   | X |   |   |
| hsa-miR-204-5p | X | X | X | X |   | X |   | X |
| hsa-miR-205-5p | X | X | X | X | X | X |   |   |
| hsa-miR-20a-5p | X | X | X | X |   |   | X |   |
| hsa-miR-210 |   |   |   |   |   | X |   |   |
| hsa-miR-222-3p | X | X | X | X | X | X |   |   |
| hsa-miR-223-3p | X | X | X | X |   | X |   |   |
| hsa-miR-22-5p | X | X | X | X |   |   |   |   |
| hsa-miR-23a-3p | X | X | X | X |   |   |   |   |

TABLE 1-continued

| All miRs | A | B | C | D | E | F | G | H |
|---|---|---|---|---|---|---|---|---|
| hsa-miR-23b-3p | X | X | X | X |   | X | X | X |
| hsa-miR-24-3p | X | X | X | X | X | X |   | X |
| hsa-miR-25-3p |   |   |   |   |   | X |   |   |
| hsa-miR-26a-5p |   |   |   |   |   |   | X | X |
| hsa-miR-27b-3p | X | X | X | X |   |   | X | X |
| hsa-miR-29a-3p | X | X | X | X |   | X |   |   |
| hsa-miR-29b-3p |   |   |   |   |   | X |   |   |
| hsa-miR-29c-3p | X | X | X | X |   | X |   |   |
| hsa-miR-30a-3p | X | X | X | X |   | X |   |   |
| hsa-miR-30a-5p | X | X | X | X |   | X |   | X |
| hsa-miR-30b-5p | X | X | X | X |   | X | X | X |
| hsa-miR-30c-5p | X | X | X | X |   | X |   | X |
| hsa-miR-30e-5p | X | X | X | X |   |   |   |   |
| hsa-miR-31-3p | X | X | X | X | X | X |   |   |
| hsa-miR-31-5p | X | X | X | X | X | X |   |   |
| hsa-miR-320a | X | X | X | X |   | X |   |   |
| hsa-miR-320b |   |   |   |   |   | X |   |   |
| hsa-miR-320c |   |   |   |   |   | X |   |   |
| hsa-miR-331-3p |   |   |   |   |   | X | X |   |
| hsa-miR-362-3p |   |   |   |   |   | X |   |   |
| hsa-miR-362-5p | X | X | X | X |   |   |   |   |
| hsa-miR-363-3p |   |   |   |   |   | X |   |   |
| hsa-miR-375 |   |   |   |   | X | X |   |   |
| hsa-miR-378a-3p | X | X | X | X | X | X |   |   |
| hsa-miR-425-3p |   |   |   |   |   | X |   |   |
| hsa-miR-425-5p |   |   |   |   |   | X |   |   |
| hsa-miR-455-3p | X | X | X | X |   |   |   |   |
| hsa-miR-490-3p |   |   |   |   |   | X |   |   |
| hsa-miR-660-5p |   |   |   |   |   | X |   |   |
| hsa-miR-93-5p | X | X | X | X |   | X |   |   |
| hsa-miR-99a-5p | X | X | X | X |   | X |   | X |
| hsa-miR-99b-5p |   |   |   |   |   |   | X | X |

Notes
X: specific miR is mentioned
A: Example 2 (discovery), Top 20 significantly regulated
B: Example 3 (Validation) Top 20 significantly regulated
C: Example 5 (Alternative discovery) Top 20 significantly regulated (tab 5)
D: Example 5 (Alternative discovery)
E: Example 8 (discovery using LASSO regression) 10 best
F: Example 5 (significantly de-regulated = tab 6)
G: normalisers in 23 assays (example 2)
H: 23 assays (example 2)

Surprisingly, we have found that as few as 20, 10, 9, 8, 7, 6, 5, 4, 3 or even 2 miRs drawn from this group of 76 miRs can be used to distinguish between patients with PC and patients with BPH with an diagnostic accuracy, which is far beyond what is offered by the standard PSA-test, see Example 2, 3, 4, 6, 8, 9, 10, 11, 12, and 13.

In general the Area Under Curve (AUC) of a ROC-curve is indicative of the diagnostic "power" of a diagnostic test. T.G. Tape has provided score for diagnostic tests, wherein
AUC: 0.90-1=excellent
AUC: 0.80-0.90=good
AUC: 0.70-0.80=fair
AUC: 0.60-0.70=poor
AUC: 0.50-0.60=fail
(ref.: Tape, Thomas G.: "Interpreting Diagnostic Tests", http://gim.unmc.edu/dxtests/Default.htm)

According to this score the diagnostic classifiers (or panels) of the invention are good to excellent.

Thus one aspect of the present invention is an in vitro method for assessing the risk that a subject suffers from prostate cancer, comprising measuring the expression level of at least two miRs selected from group of miRs consisting of: hsa-let-7a-5p, hsa-let-7b-5p, hsa-let-7c-5p, hsa-let-7e-5p, hsa-let-7f-5p, hsa-let-7g-5p, hsa-miR-100-5p, hsa-miR-106a-5p, hsa-miR-10a-5p, hsa-miR-10b-5p, hsa-miR-1238-3p, hsa-miR-125b-5p, hsa-miR-1260a, hsa-miR-130a-3p, hsa-miR-132-3p, hsa-miR-135a-5p, hsa-miR-135b-5p, hsa-miR-136-5p, hsa-miR-140-3p, hsa-miR-141-3p, hsa-miR-142-3p, hsa-miR-146a-5p, hsa-miR-148a-3p, hsa-miR-151a-3p, hsa-miR-151a-5p, hsa-miR-15b-5p, hsa-miR-16-5p, hsa-miR-191-5p, hsa-miR-1972, hsa-miR-19a-3p, hsa-miR-19b-3p, hsa-miR-200a-3p, hsa-miR-200b-3p, hsa-miR-200b-5p, hsa-miR-200c-3p, hsa-miR-203a, hsa-miR-204-5p, hsa-miR-205-5p, hsa-miR-20a-5p, hsa-miR-210, hsa-miR-222-3p, hsa-miR-223-3p, hsa-miR-22-5p, hsa-miR-23a-3p, hsa-miR-23b-3p, hsa-miR-24-3p, hsa-miR-25-3p, hsa-miR-26a-5p, hsa-miR-27b-3p, hsa-miR-29a-3p, hsa-miR-29b-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-320b, hsa-miR-320c, hsa-miR-331-3p, hsa-miR-362-3p, hsa-miR-362-5p, hsa-miR-363-3p, hsa-miR-375, hsa-miR-378a-3p, hsa-miR-425-3p, hsa-miR-425-5p, hsa-miR-455-3p, hsa-miR-490-3p, hsa-miR-660-5p, hsa-miR-93-5p, hsa-miR-99a-5p, and hsa-miR-99b-5p, in a urine sample from said subject, wherein a changed expression level of said at least 2 miRs, as compared to healthy donors, indicates an increased probability of said subject suffering from prostate cancer.

The 20 most significantly regulated miRNAs in the validation study appears especially attractive (table 20). Thus one embodiment of the present invention is an in vitro method for assessing the risk that a subject suffers from prostate cancer, comprising measuring the expression level of at least two miRs selected from group of miRs consisting of hsa-miR-141-3p, hsa-miR-142-3p, hsa-miR-146a-5p, hsa-miR-151a-3p, hsa-miR-16-5p, hsa-miR-191-5p, hsa-miR-200c-3p, hsa-miR-203a, hsa-miR-204-5p, hsa-miR-205-5p, hsa-miR-222-3p, hsa-miR-223-3p, hsa-miR-24-3p, hsa-miR-30a-5p, hsa-miR-30c-5p, hsa-miR-31-3p, hsa-miR-31-5p, hsa-miR-320a, hsa-miR-93-5p and hsa-miR-99a-5p in a urine sample from said subject, wherein a changed expression level of said at least 2 miRs, as compared to healthy donors, indicates an increased probability of said subject suffering from prostate cancer.

Measuring 76 or even 20 miRs may appear as impractically for diagnostic tests intended for everyday clinics. In Example 3 table 3 the miRNAs with strongest diagnostic potential for discrimination between cancer and non-PC controls is shown. Accordingly one further embodiment of the invention is an in vitro method for discrimination between PC and non-PC comprising measuring the expression level of at least two miRs selected from group of miRs consisting of hsa-miR-141-3p, hsa-miR-146a-5p, hsa-miR-16-5p, hsa-miR-200c-3p, hsa-miR-205-5p, hsa-miR-222-3p, hsa-miR-24-3p, hsa-miR-30a-5p, hsa-miR-30c-5p and hsa-miR-31-5p.

Likewise an embodiment of the invention is an in vitro method for wherein the least two miRs are selected from group of miRs consisting of the six best ranking miRs, i.e. hsa-miR-146a-5p, hsa-miR-16-5p, hsa-miR-200c-3p, hsa-miR-205-5p, hsa-miR-30c-5p and hsa-miR-31-5p is contemplated.

Other groups of miRs may be drawn from table 3, e.g. the group of 4 miRs consisting of hsa-miR-146a-5p, hsa-miR-31-5p, hsa-miR-24-3p and hsa-miR-30c-5p, which happens to be the 4 miRS with the highest AUC in cohort 1, the group of 3 miRs consisting of hsa-miR-30c-5p, hsa-miR-222-3p, and hsa-miR-24-3p, and the group of 3 miRs consisting of hsa-miR-30a-5p, hsa-miR-222-3p, and hsa-miR-24-3p.

Further analysis showed that also 5 and 4 miRs drawn from the group of miRs result in classifiers with a diagnostic power (AUC of a ROC-curve) similar to or better than the standard total prostate specific antigen (PSA) test.

Accordingly, we here provide an in vitro method for assessing the risk that a subject suffers from prostate cancer, comprising measuring the expression level of at least 2, 3, 4, 5, 6, 7 or more, 10 or more or 20 miRs selected from group of miRs consisting of consisting of: hsa-let-7a-5p, hsa-let-7b-5p, hsa-let-7c-5p, hsa-let-7e-5p, hsa-let-7f-5p, hsa-let-7g-5p, hsa-miR-100-5p, hsa-miR-106a-5p, hsa-miR-10a-5p, hsa-miR-10b-5p, hsa-miR-1238-3p, hsa-miR-125b-5p, hsa-miR-1260a, hsa-miR-130a-3p, hsa-miR-132-3p, hsa-miR-135a-5p, hsa-miR-135b-5p, hsa-miR-136-5p, hsa-miR-140-3p, hsa-miR-141-3p, hsa-miR-142-3p, hsa-miR-146a-5p, hsa-miR-148a-3p, hsa-miR-151a-3p, hsa-miR-151a-5p, hsa-miR-15b-5p, hsa-miR-16-5p, hsa-miR-191-5p, hsa-miR-1972, hsa-miR-19a-3p, hsa-miR-19b-3p, hsa-miR-200a-3p, hsa-miR-200b-3p, hsa-miR-200b-5p, hsa-miR-200c-3p, hsa-miR-203a, hsa-miR-204-5p, hsa-miR-205-5p, hsa-miR-20a-5p, hsa-miR-210, hsa-miR-222-3p, hsa-miR-223-3p, hsa-miR-22-5p, hsa-miR-23a-3p, hsa-miR-23b-3p, hsa-miR-24-3p, hsa-miR-25-3p, hsa-miR-26a-5p, hsa-miR-27b-3p, hsa-miR-29a-3p, hsa-miR-29b-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-320b, hsa-miR-320c, hsa-miR-331-3p, hsa-miR-362-3p, hsa-miR-362-5p, hsa-miR-363-3p, hsa-miR-375, hsa-miR-378a-3p, hsa-miR-425-3p, hsa-miR-425-5p, hsa-miR-455-3p, hsa-miR-490-3p, hsa-miR-660-5p, hsa-miR-93-5p, hsa-miR-99a-5p, and hsa-miR-99b-5p, in a urine sample from said subject.

In further embodiments of the invention said at least 2, 3, 4, 5 or more, 10 or more or 20 miRs are selected from group of miRs consisting of: hsa-miR-10b-5p, hsa-miR-135b-5p, hsa-miR-140-3p, hsa-miR-141-3p, hsa-miR-142-3p, hsa-miR-146a-5p, hsa-miR-151a-3p, hsa-miR-16-5p, hsa-miR-191-5p, hsa-miR-19a-3p, hsa-miR-200b-3p, hsa-miR-200c-3p, hsa-miR-203a, hsa-miR-204-5p, hsa-miR-205-5p, hsa-miR-20a-5p, hsa-miR-222-3p, hsa-miR-223-3p, hsa-miR-23a-3p, hsa-miR-23b-3p, hsa-miR-24-3p, hsa-miR-27b-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-362-5p, hsa-miR-378a-3p, hsa-miR-93-5p and hsa-miR-99a-5p,
or from the group of miRs consisting of: hsa-miR-141-3p, hsa-miR-142-3p, hsa-miR-146a-5p, hsa-miR-151a-3p, hsa-miR-16-5p, hsa-miR-191-5p, hsa-miR-200c-3p, hsa-miR-203a, hsa-miR-204-5p, hsa-miR-205-5p, hsa-miR-222-3p, hsa-miR-223-3p, hsa-miR-24-3p, hsa-miR-30a-5p, hsa-miR-30c-5p, hsa-miR-31-3p, hsa-miR-31-5p, hsa-miR-320a, hsa-miR-93-5p and hsa-miR-99a-5p.

Much to the inventors surprise two of the best classifiers comprise only three selected miRs namely 1) hsa-miR-30c-5p, hsa-miR-222-3p, and hsa-miR-24-3p, and 2) hsa-miR-30a-5p, hsa-miR-222-3p, and hsa-miR-24-3p (see example 11, 12, and 13) making these two signatures preferred embodiments of the invention.

Even a classifier comprising only two selected miRs namely hsa-miR-30c-5p and hsa-miR-31-5p (see example 2, 3 and 4) appear advantageous. In addition to its ability to discriminate between PC and controls with very high specificity and sensitivity this classifier appears extraordinarily robust and not depending on the particular method for sampling and detection of miR levels, see example 4.

In the present context the terms "expression level of a miR", "miR expression level" and "level of a miR" are used synonymously as a measure of the "amount of a specific miR" that is detected in the sample. The "amount of a specific miR" may be expressed in either absolute, relative or normalised measures and refers to values obtained by both quantitative, as well as qualitative methods. However, as an alternative to making determinations based on the absolute expression level of the miRs, determinations may be based on the normalised expression levels of the miRs. Expression levels are normalised by correcting the absolute expression level of a miR by comparing its expression to the expression of a gene that is constitutively or nearly constitutively expressed. Suitable genes often used for normalisation include housekeeping genes such as the actin gene.

Accordingly, in one embodiment of the invention the expression levels are normalized expression levels. In the present study we use a collection of miRs for normalizing. Preferably the top 3 or top 5 most stable miRNAs from Normfinder is used to calculate a mean normalization value for each sample. Thus the normalization is performed by calculating a mean normalization value of 3 miRs being: hsa-miR-200b-3p, hsa-miR-27b-3p, and hsa-miR-30b-5p or 5 miRs being: hsa-miR-20a-5p, hsa-miR-30b-5p, hsa-let-7a-5p, hsa-miR-27b-3p, hsa-miR-23b-3p. The 3 miR-normaliser is preferred.

One of the reasons that the standard total prostate specific antigen (tPSA) test is so widespread used for screening purposes is that it is based on minimal invasive procedures (blood testing).

Although the tPSA only require blood testing it nevertheless demand that the test person must visit a hospital, clinic or health professional, who can take the blood sample. In comparison testing on urine seem advantageous. However, urine contains only miniscule amounts of miRs. In the present invention this challenge was overcome by 1) measuring the expression level of said miRs in an exosome preparation, prepared form an urine sample and 2) measuring the expression level of miRs by Exiqons sensitive method of Q-PCR—the UniRT method, see: Example 1 and 7, Accordingly the UniRT method is a preferred method of Q-PCR.

Whereas standard urine samples are preferred from a screening point of view literature provide examples that urine samples obtained after prostatic massage may be advantageous, see eg. (19). Example 4 is performed on urine samples obtained after prostatic massage. In example 4 it is shown that the 2-miR classifier (miR-30c, miR-31-5p) possess a diagnostic power that by far outrange the diagnostic power of the standard total prostate specific antigen (tPSA) test. The 2-miR classifier performed surprisingly well with an area (AUC) under the ROC curve of 0.79 (CI: 0.69 to 0.90, $p<<0.0001$) and a sensitivity of 72.9% and specificity of 84.8%, using a the cut-off value established in cohort 1.

Accordingly in one embodiment of the invention the urine sample is from a subject who have been subjected to prostatic massage immediately before the urine was sampled.

When applying a diagnostic assay in practice it is advantageous to use the assay values to calculate a diagnostic diagnostic score (S) allowing one to define cut-off values and to differentiate between cancer and non-cancer samples based on the diagnostic diagnostic score. Thus one embodiment of the present invention is a method, wherein the assessment of the risk that a subject suffers from prostate cancer involves detecting the level of said at least two miRs in said sample and calculate a diagnostic diagnostic score (S) based on a dataset comprising the expression level data of said at least two miRs.

The level of miRs may conveniently be quantified by Quantitative real-time Reverse Transcriptase mediated Polymerase Chain Reaction method, RT-QPCR (13).

One particularly preferred measure of the "amount of a specific miR" is the Crossing point (Cp) value obtained by real-time qRT-PCR. Another preferred measure of the "amount of a specific miR" is the "threshold cycle value (Ct)" value likewise obtained by real-time qRT-PCR as described in the examples. The Cp and the Ct measures of the "amount of a specific miR" provide roughly similar measures, see (13). Whether to choose Cp or Ct is largely a matter of choice of the machine the assay tied to and performed on. If the amplification is performed in a Light-Cycler® 480 Real-Time PCR System using the Roche LC software the amount of a specific miR is expressed by the Cp. If the amplification is performed in Applied Biosystems ABI Prism 7900HT 384-well instrument using the software provided with it the amount of a specific miR is expressed by the Ct. The following refer to the Cp-value but apply as well to the Ct-value and to the "quantification cycle" (Cq) value.

The Cp-value is related to the level of e.g. a specific miR, by the relation:

(liniar) expression level of miRx~$2^{-Cp(miRx)}$

Wherein Cp(miRx) designates the Cp-readout from real-time QPCR instrument specifically detecting one specific miR called miRx. Example 2 describes such an assay in details.

Accordingly, when the Cp-values are used as quantifiers of miR-levels, eg. the expression:

$$\frac{(\text{level of } miR31) \times (\text{level of } miR146) \times (\text{level of } miR24)}{(\text{level of } miR30c)}$$

is equivalent to:

$+Cp(miR31)+Cp(miR146)+Cp(miR24)-Cp(miR30c)$ and likewise the expression:

$$\frac{(\text{level of } miR31)}{(\text{level of } miR30c)}$$

is equivalent to:

$+Cp(miR31)-Cp(miR30c)$

Accordingly, a useable estimator—diagnostic diagnostic score (S)—for the 4-miR classifier (hsa-miR-31-5p, hsa-miR-146a-5p, hsa-miR-30c-5p and hsa-miR-24-3p) is a linear regression model, such as:

$X \times Cp(miR31)+Y \times Cp(miR146)+Z \times Cp(miR24)+W \times Cp(miR30c)$ where the coefficients X, Y, Z and W are determined by the regression-analysis according to the particular set-up.

Similarly, an estimator—diagnostic diagnostic score (S)—for the 2-miR classifier is $X \times Cp(miR31)+Y \times Cp(miR30c)$ where the coefficients X and Y are determined by the regression-analysis. Both linear and other types of regression are contemplated.

Therefore in one embodiment of the invention the diagnostic diagnostic score (S) is calculated as follows:

$S=X*C(\text{hsa-miR-30c-5p})+Y*C(\text{hsa-miR-31-5p})$ wherein "C" is the threshold cycle value (Ct) or the crossing point value (Cp), and wherein X and Y are coefficients determined by linear or another type of regression.

By "machine learning" is referred to a process which take advantage of computer algorithms that improve automatically through experience, in the art this process of improving the algorithms is often referred to as "training". Machine learning can be used to discover general rules in large data sets, machine learning can e.g. be used to extract clinical informative data from a dataset comprising miR expression in cancer and non-cancer samples of the prostate. A general treatise of the concept of machine learning can be found in (21) which hereby is incorporated herein by reference. Accordingly in one embodiment of the invention the algorithm for calculating the diagnostic diagnostic score (S) was reached applying machine learning.

Surprisingly, as shown in the examples even simple estimators based on ratios such as:

$$S = \frac{(\text{level of } miR24-3p)(\text{level of } miR222-3p)}{(\text{level of } miR30c-5p)^2},$$

$$S = \frac{(\text{level of } miR24-3p)(\text{level of } miR222-3p)}{(\text{level of } miR30a-5p)^2}$$

or:

$$S = \frac{(\text{level of } miR31)}{(\text{level of } miR30c)}$$

has a diagnostic feature which by far outrange the diagnostic power of the standard total prostate specific antigen (tPSA) test, and furthermore has the advantage to make normalization unnecessary, thus further simplifying the assay.

Accordingly, favorable embodiments of the invention are methods comprising that the diagnostic score S is calculated as a ratio of the expression level of miRs, e.g. the ratio of the expression level of hsa-miR-24-3p and hsa-miR-222-3p vs. the expression level of hsa-miR-30a-5p, the ratio of the expression level of hsa-miR-24-3p and hsa-miR-222-3p vs. the expression level of hsa-miR-30c-5p, or the ratio of the expression level of hsa-miR-30c-5p vs. the expression level of hsa-miR-31-5p.

As discussed in the ratio between hsa-miR-31-5p and hsa-miR-30c-5p perform surprisingly well with an AUC of 89.9% in the discovery cohort (Example 5). As illustrated in example 11, 12 and 13 the two three-miR ratio-based classifiers: hsa-miR-24-3p, hsa-miR-222-3p over hsa-miR-30a-5p, and the hsa-miR-24-3p, hsa-miR-222-3p over hsa-miR-30c-5p, performed even better, showing AUCs in the validations close to or even over 0.9, Accordingly in further embodiments of the invention the diagnostic diagnostic score (S) is calculated as:

$S=C(\text{hsa-miR-24-3p})+C(\text{hsa-miR-222-3p})-(2 \times C(\text{hsa-miR-30a-5p}))$ wherein "C" is the threshold cycle value (Ct) or the crossing point value (Cp) obtained by quantitative real-time PCR (qRT-PCR) for hsa-miR-24-3p, hsa-miR-222-3p and hsa-miR-30a-5p, respectively.

or as:

$S=C(\text{hsa-miR-24-3p})+C(\text{hsa-miR-222-3p})-(2 \times C(\text{hsa-miR-30c-5p}))$ wherein "C" is the threshold cycle value (Ct) or the crossing point value (Cp) obtained by quantitative real-time PCR (qRT-PCR) for hsa-miR-24-3p, hsa-miR-222-3p and hsa-miR-30c-5p, respectively.

Nevertheless, in example 5 a number of other surprisingly well performing 2-miR ratios are mentioned, se Example 5 table 7, Also these ratio-based biomarkers are considered as embodiments of the invention.

A particularly interesting embodiment of the invention relate to the group of patients characterized by that a previous standard prostate specific antigen (PSA) measurement has indicated that their serum PSA level is below 10 ng/mL.

This group is perhaps the most interesting because their PSA-testing puts them into a "gray-zone" with respect to further invasive testing. Accordingly, these patients would greatly benefit from a test that could supplement the PSA test.

Surprisingly, the two three-mirs classifiers were even more successful when validated on the sub-population of patients with PSA levels below 10 ng/mL (Example 10).

In particularly the hsa-miR-30c-5p, hsa-miR-222-3p, and hsa-miR-24-3p classifier is noteworthy with a AUC=0.91 when performed on the validation cohort (see example 13).

Thus the hsa-miR-30c-5p, hsa-miR-222-3p, and hsa-miR-24-3p classifier with the diagnostic score (S)=C(hsa-miR-24-3p)+C(hsa-miR-222-3p)−(2×C(hsa-miR-30c-5p)), wherein "C" is the threshold cycle value (Ct) or the crossing point value (Cp) obtained by quantitative real-time PCR (qRT-PCR) specific for the miR, is the preferred embodiment of the invention.

Furthermore the hsa-miR-30c-5p, hsa-miR-222-3p, and hsa-miR-24-3p classifier proves to be remarkable robust. To investigate the robustness of the three-miR classifier we applied the assay to yet an independent cohort (cohort 3) where specimens were sampled and processed with a considerably different methodology than cohort 5 and 6 (Example 14). Interestingly, the hsa-miR-30c-5p, hsa-miR-222-3p, and hsa-miR-24-3p classifier was also successfully validated in this cohort (Example 14).

In one aspect the invention relate to a method of treating a patient in need of prostate cancer treatment, the method comprising: performing a diagnostic test according to any of the preceding claims to determine if the patient have an increased probability of suffering from prostate cancer, and selecting an appropriate therapy for the patient based on this Information.

A further aspect of the invention is a kit of parts for in vitro assessment of the risk that a subject suffers from prostate cancer, comprising aliquots of the reagents needed for measuring the expression level the level of at least two miRs selected from group of miRs consisting of: hsa-let-7a-5p, hsa-let-7b-5p, hsa-let-7c-5p, hsa-let-7e-5p, hsa-let-7f-5p, hsa-let-7g-5p, hsa-miR-100-5p, hsa-miR-106a-5p, hsa-miR-10a-5p, hsa-miR-10b-5p, hsa-miR-1238-3p, hsa-miR-125b-5p, hsa-miR-1260a, hsa-miR-130a-3p, hsa-miR-132-3p, hsa-miR-135a-5p, hsa-miR-135b-5p, hsa-miR-136-5p, hsa-miR-140-3p, hsa-miR-141-3p, hsa-miR-142-3p, hsa-miR-146a-5p, hsa-miR-148a-3p, hsa-miR-151a-3p, hsa-miR-151a-5p, hsa-miR-15b-5p, hsa-miR-16-5p, hsa-miR-191-5p, hsa-miR-1972, hsa-miR-19a-3p, hsa-miR-19b-3p, hsa-miR-200a-3p, hsa-miR-200b-3p, hsa-miR-200b-5p, hsa-miR-200c-3p, hsa-miR-203a, hsa-miR-204-5p, hsa-miR-205-5p, hsa-miR-20a-5p, hsa-miR-210, hsa-miR-222-3p, hsa-miR-223-3p, hsa-miR-22-5p, hsa-miR-23a-3p, hsa-miR-23b-3p, hsa-miR-24-3p, hsa-miR-25-3p, hsa-miR-26a-5p, hsa-miR-27b-3p, hsa-miR-29a-3p, hsa-miR-29b-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-320b, hsa-miR-320c, hsa-miR-331-3p, hsa-miR-362-3p, hsa-miR-362-5p, hsa-miR-363-3p, hsa-miR-375, hsa-miR-378a-3p, hsa-miR-425-3p, hsa-miR-425-5p, hsa-miR-455-3p, hsa-miR-490-3p, hsa-miR-660-5p, hsa-miR-93-5p, hsa-miR-99a-5p, and hsa-miR-99b-5p, in a urine sample from said subject, wherein a changed expression level of said at least 2 miRs, as compared to healthy donors, indicates an increased probability of said subject suffering from prostate cancer.

Further embodiments of the invention is a kit, wherein the at least two miRs are selected from the group of miRs consisting of: hsa-miR-141-3p, hsa-miR-142-3p, hsa-miR-146a-5p, hsa-miR-151a-3p, hsa-miR-16-5p, hsa-miR-191-5p, hsa-miR-200c-3p, hsa-miR-203a, hsa-miR-204-5p, hsa-miR-205-5p, hsa-miR-222-3p, hsa-miR-223-3p, hsa-miR-24-3p, hsa-miR-30a-5p, hsa-miR-30c-5p, hsa-miR-31-3p, hsa-miR-31-5p, hsa-miR-320a, hsa-miR-93-5p and hsa-miR-99a-5p, or wherein the at least two miRs are selected from the group of miRs consisting of: hsa-miR-141-3p, hsa-miR-146a-5p, hsa-miR-16-5p, hsa-miR-200c-3p, hsa-miR-205-5p, hsa-miR-222-3p, hsa-miR-24-3p, hsa-miR-30a-5p, hsa-miR-30c-5p and hsa-miR-31-5p, or wherein the at least two miRs are selected from the group of miRs consisting of: hsa-miR-141-3p, hsa-miR-16-5p, hsa-miR-222-3p, hsa-miR-24-3p, hsa-miR-31-3p, hsa-miR-31-5p, and hsa-miR-331-3p, or wherein the at least two miRs are selected from the group of miRs consisting of: hsa-miR-146a-5p, hsa-miR-16-5p, hsa-miR-200c-3p, hsa-miR-205-5p, hsa-miR-30c-5p and hsa-miR-31-5p.

In particularly a kit, wherein the at least two selected miRs are: hsa-miR-30c-5p, hsa-miR-222-3p, and hsa-miR-24-3p is preferred.

Probably due to RNases the abundance of free (i.e. not in cells or particles) microRNAs in biofluids such as standard urine samples are very low. However, microRNAs have been shown to be stabilized and protected from RNase degradation by inclusion in various protein complexes and membranous particles such as exosomes or microvesicles.

Accordingly, in the a preferred embodiment of the present invention the miRs are extracted from an exosome preparation of the urine sample.

And consequently, a preferred kit according to the invention comprises reagents needed to obtain the exosome preparation of the urine sample.

The invention is further illustrated in the following non-limiting examples and the figures

LEGENDS

FIG. 1: The ROC curves for the 2 miR classifier composed of the ratio of miR-31-5p vs. miR-30c. FIG. 1A is the ROC curve for cohort 1 (discovery cohort), FIG. 1B is the ROC curve for cohort 2 (validation cohort, Example 3), and FIG. 1C is the ROC curve for cohort 3 (validation cohort, Example 4).

FIG. 2: The ROC curve for the 20 miRNAs presented in example 5, table 5, Sensitivity and specificity is given below the curve.

Figure 3:
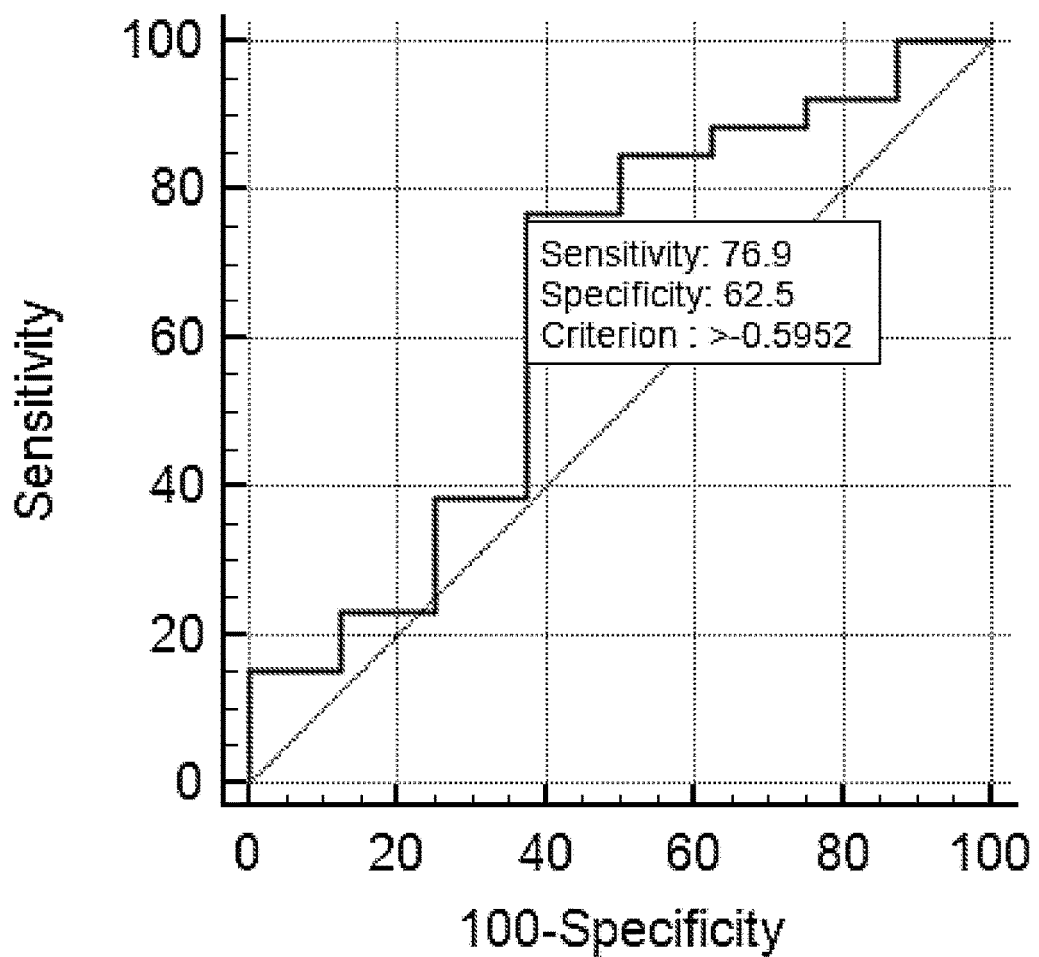

FIG. 3: 2 miR classifier for PC diagnosis applied on bladder cancer vs. controls (miR31-5p-miR30c-5p).

Figure 4:
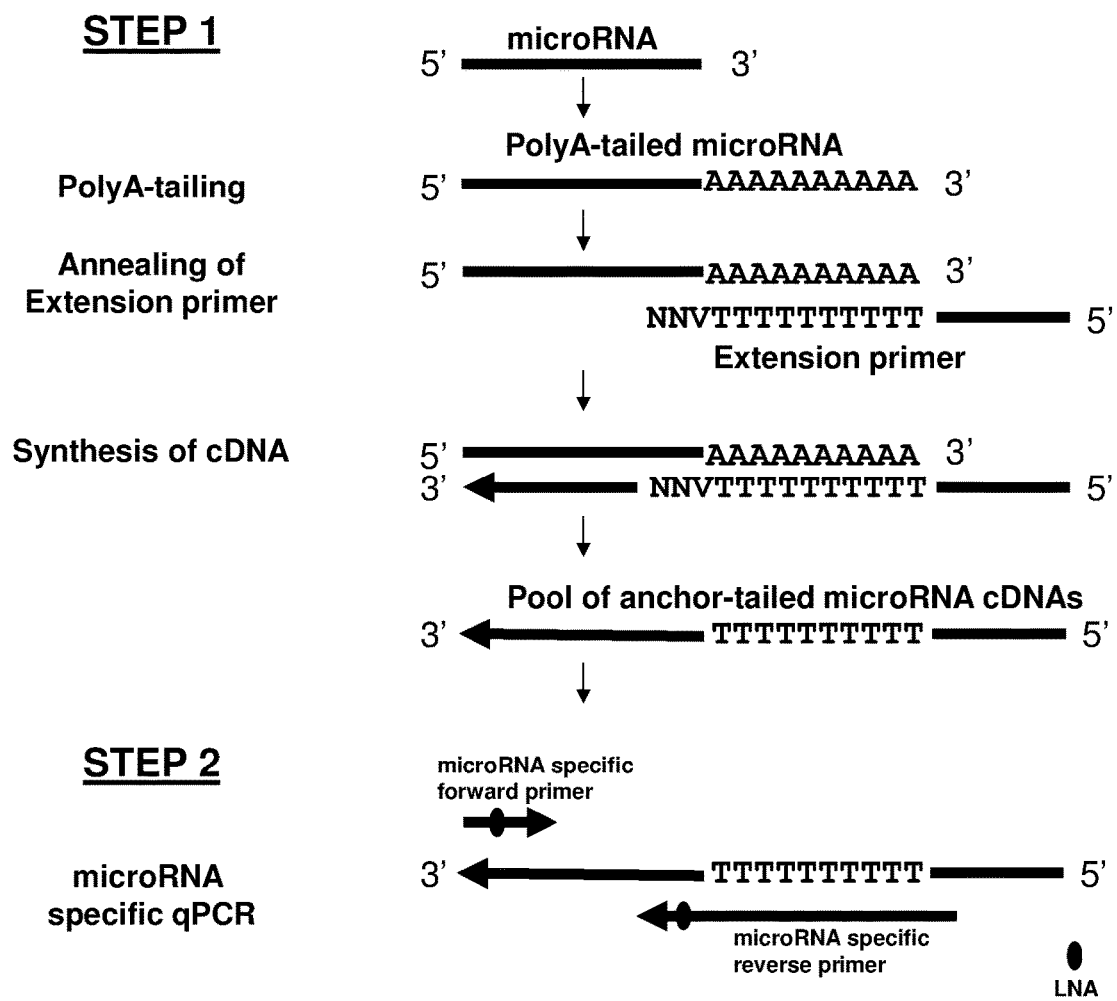

FIG. 4: The UniRT method.

Figure 5:
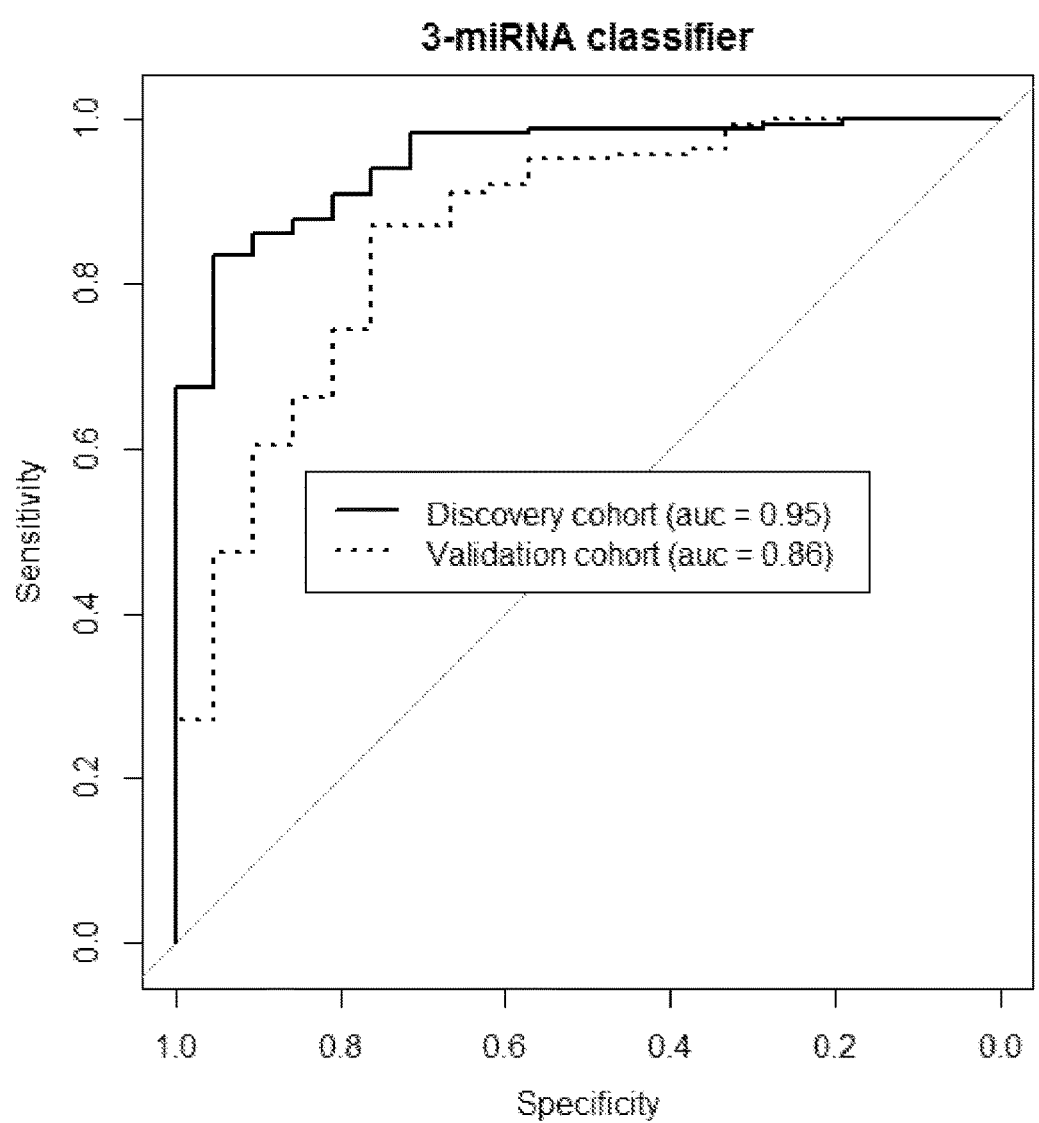

FIG. 5: ROC curve of 3 miR panel classifier in discovery and validation cohorts (cohort 4 and 5).

Figure 6:
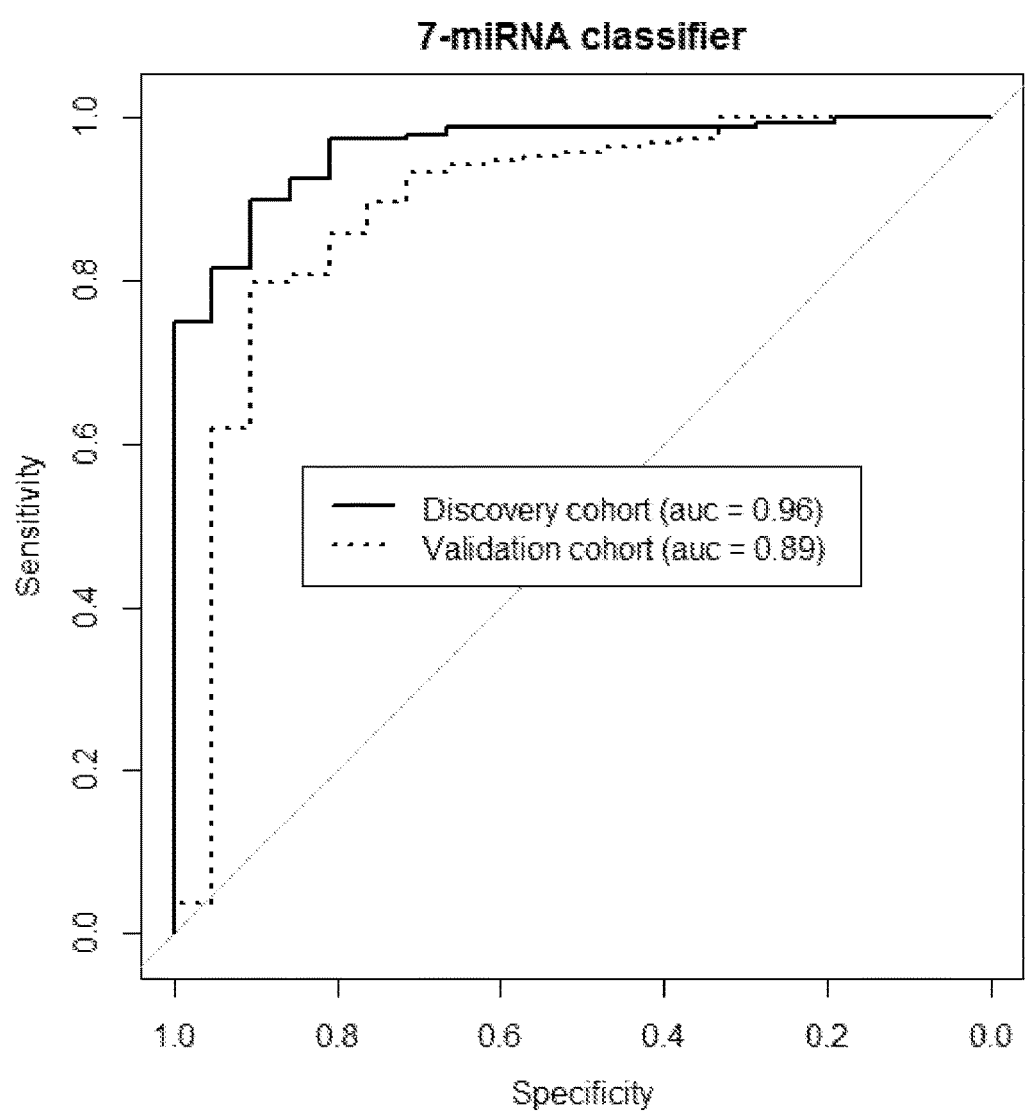

FIG. 6: ROC curve of 7miR panel classifier (hsa-miR-141-3p, hsa-miR-16-5p, hsa-miR-222-3p, hsa-miR-24-3p, hsa-miR-31-3p, hsa-miR-31-5p, and hsa-miR-331-3p) in the discovery and validation cohorts (cohort 4 and 5).

FIG. 7a: ROC curve of 3miR_1 ratio based classifier (hsa-miR-24-3p, hsa-miR-222-3p, hsa-miR-30a-5p) in the discovery cohort, cohort 4.

Figure 7B:
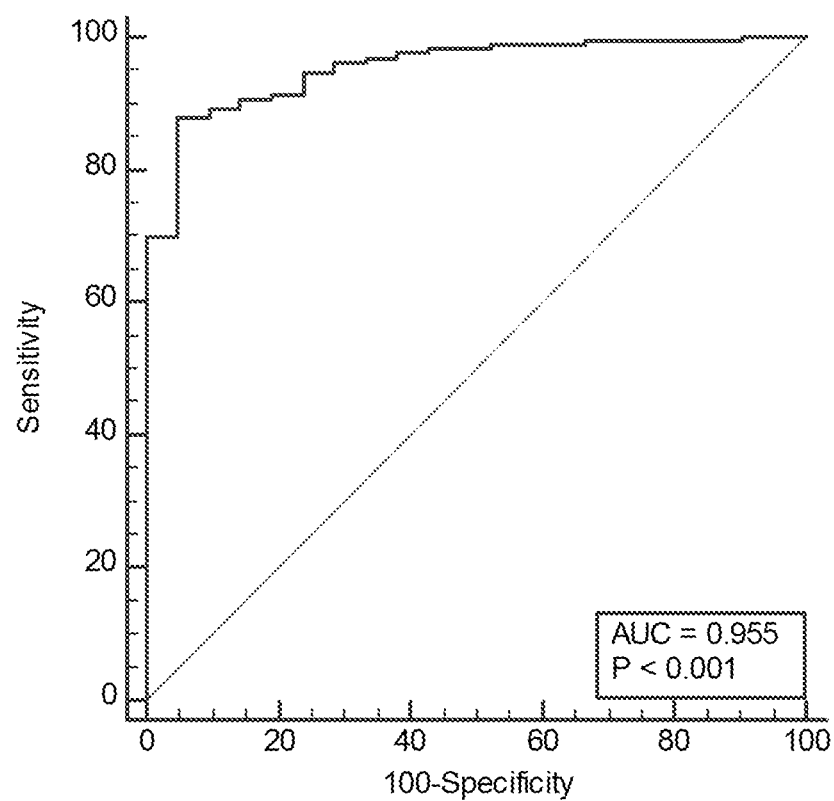

FIG. 7b: ROC curve of 3miR_2 ratio based classifier (hsa-miR-24-3p, hsa-miR-222-3p, hsa-miR-30c-5p) in the discovery cohort, cohort 4.

Figure 8A:
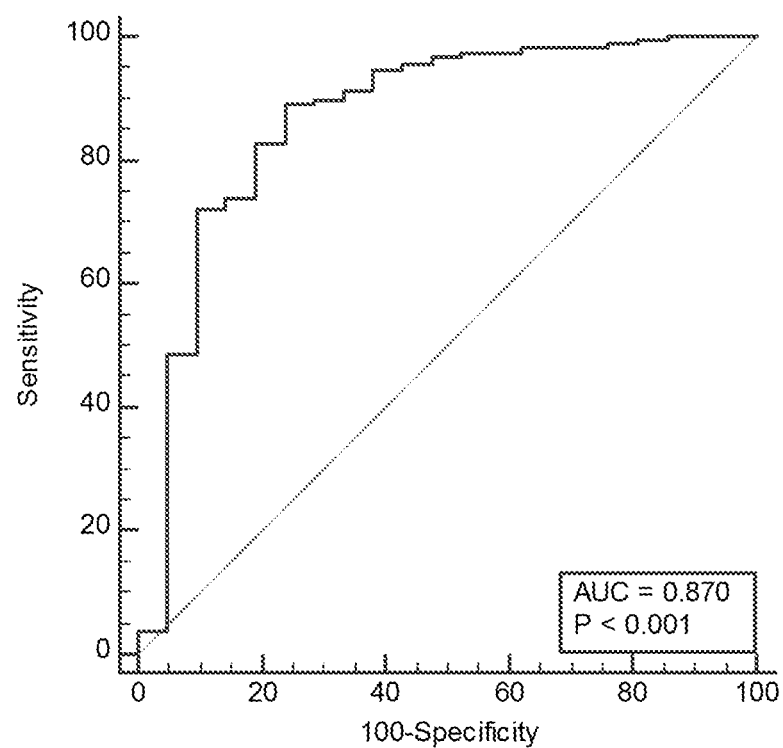

FIG. 8a: ROC curve of 3miR_1 (hsa-miR-24-3p, hsa-miR-222-3p, hsa-miR-30a-5p) ratio based biomarker signature in validation cohort (cohort 5).

Figure 8B:
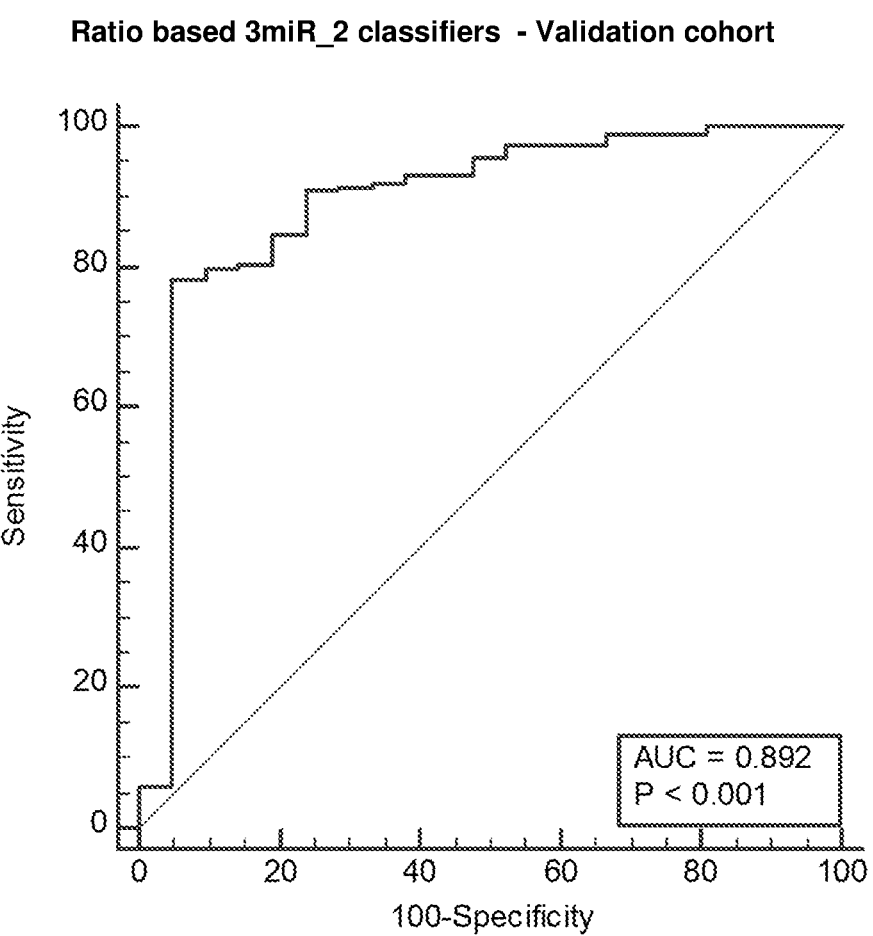

FIG. 8b: ROC curve of 3miR_2 (hsa-miR-24-3p, hsa-miR-222-3p, hsa-miR-30c-5p) ratio based classifier in validation cohort (cohort 5).

Figure 9A:
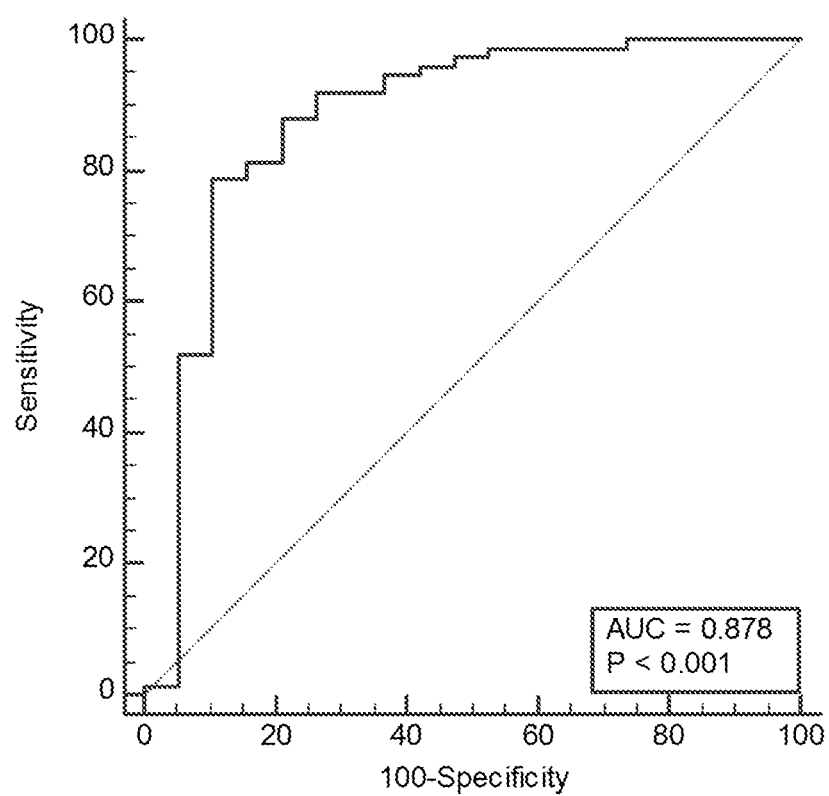

FIG. 9a: ROC curve of 3miR_1 ratio based biomarker signature in sub-set of validation cohort 5 (<10 ng/mL).

Figure 9B:
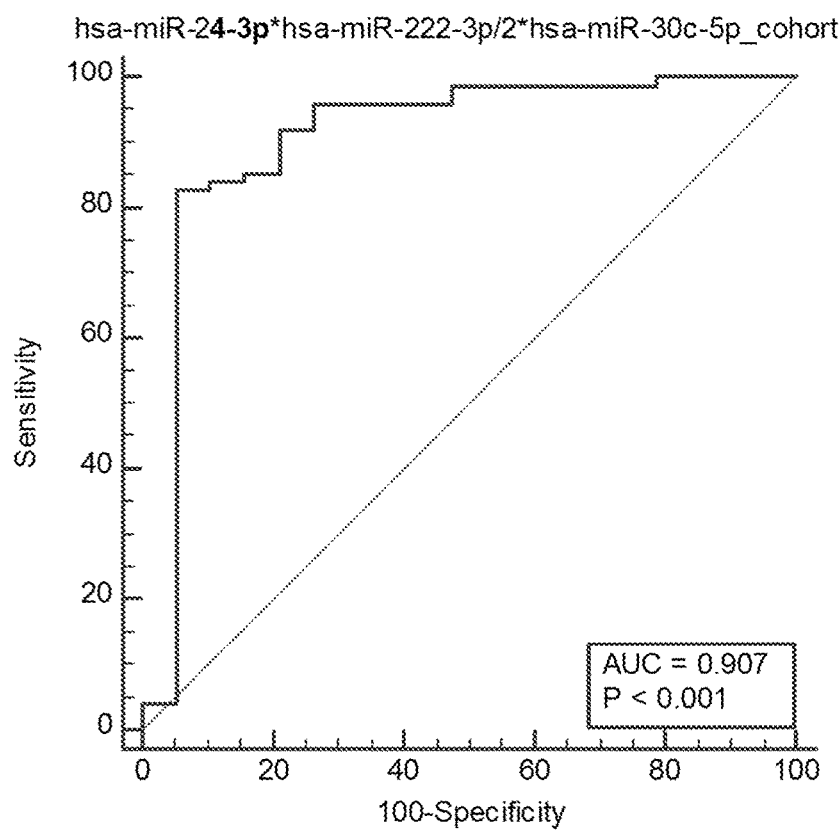

FIG. 9b: ROC curve of 3miR_2 ratio based biomarker signature in sub-set of validation cohort (cohort 5).

Figure 10:
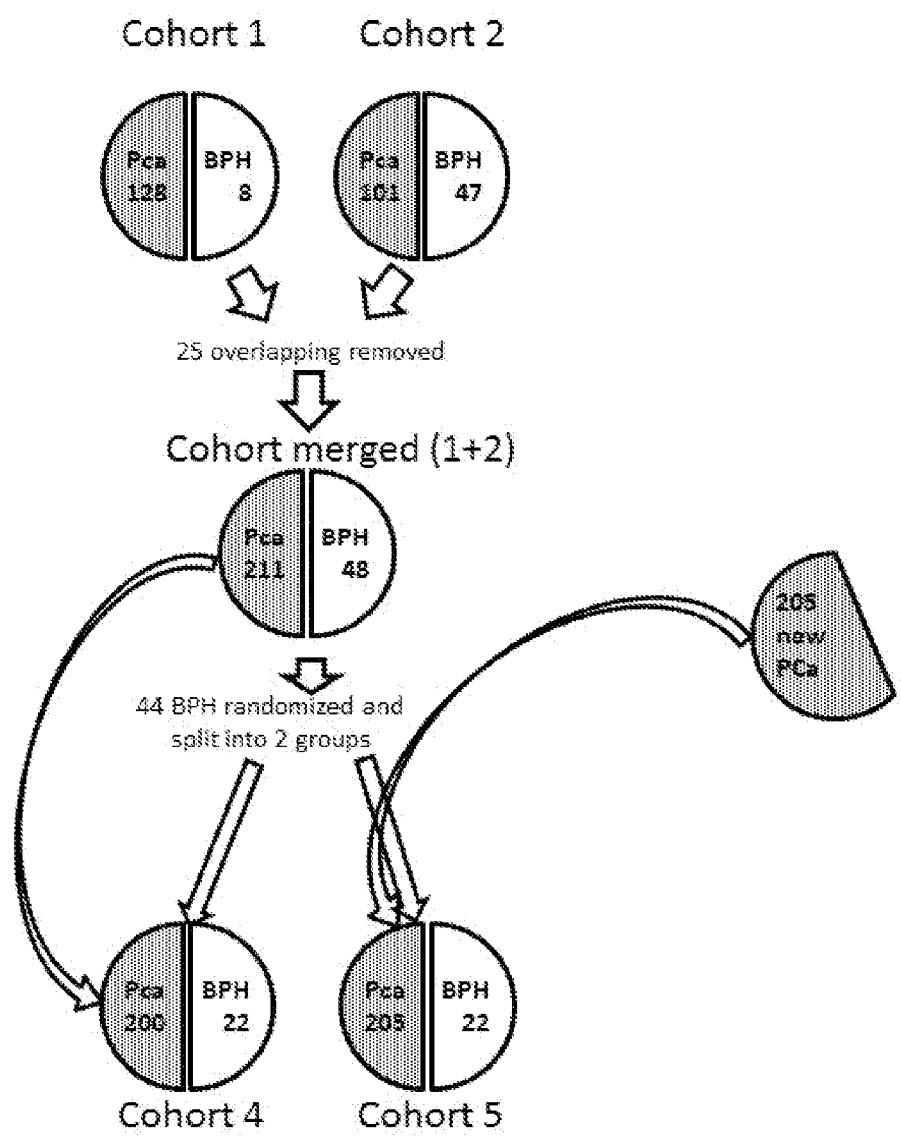

FIG. 10: overview of "Danish" cohorts.

Figure 11:
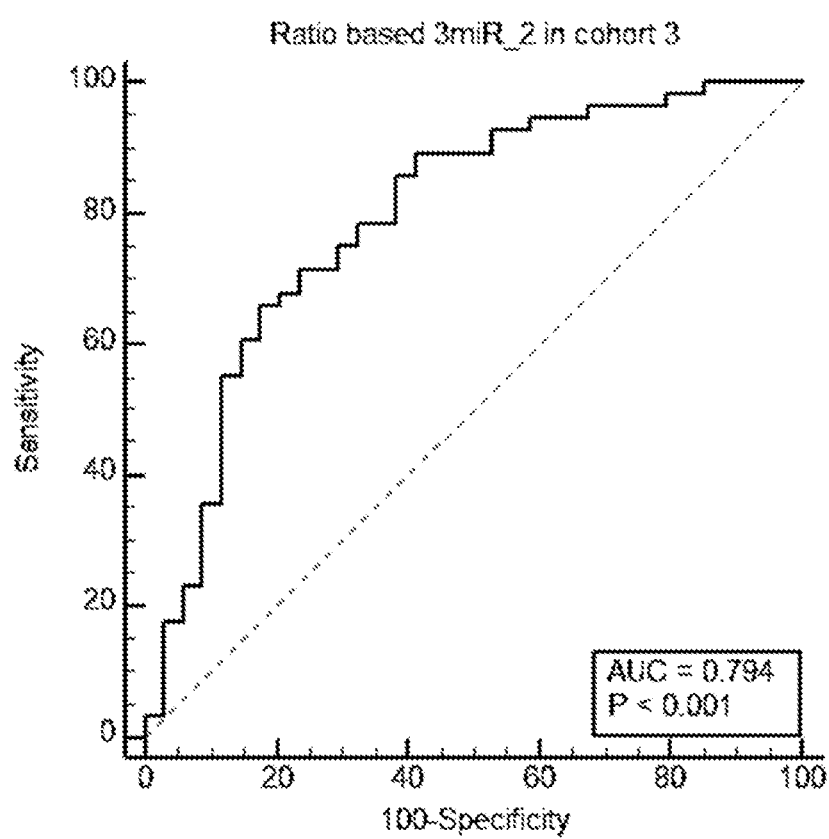

FIG. 11: ROC curve of 3miR_2 (hsa-miR-24-3p, hsa-miR-222-3p, hsa-miR-30c-5p) ratio based classifier validation in cohort 3.

EXAMPLE 1

Title: Pilot Study—microRNA Profiling in Exosome Fractionated Cell Free Urine
Aim of Study
To identify abundant microRNAs present in cell free urine samples from healthy individuals and prostate cancer patients (across different disease stages).
Specimens
All samples were collected at Department of Urology, Aarhus University Hospital, Denmark (from 1997-2005). The sample set consisted of duplicates of 12 non-malignant samples (NM; from Benign Prostate Hyperplasia (BPH) patients (controls), 33 patients sampled before undergoing curatively intended radical prostatectomy (RP) for histologically verified clinically localized PC (RP), and 8 patients with castration resistant PC (CRPC). 34 of these samples belongs to cohort 1 (Example 2).
Method
Sample Preparation
Urine samples were spun down and 4.5 ml supernatant were transferred to 5 mL CRYO tube and stored at −80° C. until use. RNA from exosomes were extracted from 3 ml urine supernatant using the miRCURY™ RNA Isolation Kit (Catalog no. 300102)—Exosome Isolation in combination with miRCURY™ RNA Isolation Kits—Cell & Plant (Catalog no. 300110), both from Exiqon, in accordance to manufacturer's instructions. The purified RNA was stored at −80° C. until use.
MicroRNA Expression Profiling
Profiling was performed using the miRCURY LNA™ Universal RT microRNA PCR platform from Exiqon in duplicates (two separate reverse transcription reactions). All the quantitative reverse transcription polymerase chain reactions (qRT-PCR) experiments and data quality controls were performed by Exiqon Services, Vedbaek, Denmark. In brief, 2 μl RNA was reverse transcribed (RT) in 10 μl reactions using the miRCURY LNA™ microRNA PCR, Universal cDNA Synthesis Kit II (Catalog no 203301). cDNA was diluted 100× and 2 μl was used as input for 10 μl PCR reactions. Relative microRNA levels were analyzed using microRNA Ready-to-Use PCR, Human panel I+II, V3, R, in 384-well PCR plates, catalog no. 203611/203612), assaying 752 different microRNAs. Note that what was previously referred to as "hsa-miR-210" relating to the nomenclature in miRBase (version 19), should be referred to as "hsa-miR-210-3p" to take the nomenclature of miRBAse (version 21) into account. Same issue apply to "hsa-let-7c" and "hsa-let-7c-5p"; and hsa-miR-203a and hsa-miR-203a-3p. An overview of the miRs of the present invention their names and their sequence is presented in table 11, For all analyses, ExiLENT SYBR® Green master mix (Catalog no. 203421) was used. Negative controls excluding RNA template from the reverse transcription reaction was performed and profiled in parallel. The amplification was performed in a LightCycler® 480 Real-Time PCR System (Roche). The amplification curves were analyzed using the Roche LC software, both for determination of quantification cycle (Cp) value and for melting curve analysis.
Result:
All assays for which the average Cp values were below 36 and detected in at least 2 samples were included for further analysis. 183 microRNAs were selected for the discovery study (Example 2).

EXAMPLE 2

Title: Identification of Diagnostic Classifier that Discriminates Between Healthy Controls and PC Cases
Aim
To identify microRNAs with diagnostic biomarker potential in urine samples from prostate cancer patients (PC) and healthy controls.
Specimens
All urine samples were collected at Department of Urology, Aarhus University Hospital, Denmark (from 1997-2005). The training cohort (cohort 1) consisted of 8 non-malignant samples (NM; from BPH patients (controls), 122 samples from patients who have undergone curatively intended RPs of histologically verified clinically localized PC 5 Castration Resistant Prostate Cancer (CRPC). See table 2 for overview of sample composition of cohorts.

TABLE 2

Patient composition of cohorts 1 and 2.

| | Cohort 1 | Cohort 2 | Merged Discovery Cohort (1 + 2) |
|---|---|---|---|
| BPH | 8 | 47 | 48 |
| CRPC | 5 | 3 | 5 |
| RP | 122 | 98 | 205 |
| RP + postEnd | 1 | 0 | 1 |

Method
Sample Preparation
Urine samples were spun down and 4.5 ml supernatant were transferred to 5 mL CRYO tube and stored at −80° C. until use. RNA from exosomes were extracted from 3 ml urine supernatant using the miRCURY™ RNA Isolation Kit (Catalog no. 300102)—Exosome Isolation in combination with miRCURY™ RNA Isolation Kits—Cell & Plant (Catalog no. 300110), both from Exiqon, in accordance to manufacturer's instructions. The purified RNA was stored at −80° C. until use.
MicroRNA Expression Profiling
Profiling was performed in singlet using the miRCURY LNA™ Universal RT microRNA PCR platforms from Exiqon. All the quantitative reverse transcription polymerase chain reactions (qRT-PCR) experiments and data quality controls were performed by Exiqon, Vedbaek, Denmark. In brief, 2 μl total RNA was reverse transcribed (RT) in 10 μl reactions using the miRCURY LNA™ microRNA PCR, Universal cDNA Synthesis Kit II (Catalog no 203301). cDNA was diluted 100× and 2 µl was analyzed in 10 µl PCR reactions. For cohort 1, relative microRNA levels were analyzed using a microRNA Ready-to-Use PCR, Pick-&-Mix microRNA PCR Panel (custom made; item no 20381) consisting of the 183 selected microRNA assays (Example 1) and 4 spike-in controls, 384-well. For all analyses, ExiLENT SYBR® Green master mix (Catalog no. 203421). Negative controls excluding RNA template from the reverse transcription reaction were performed and profiled in parallel. The amplification was performed in a LightCycler® 480 Real-Time PCR System (Roche). The amplification curves were analyzed using the Roche LC software, both for determination of quantification cycle (Cp) value and for melting curve analysis. MicroRNAs for which all Cp values exceeded 37 in all samples were excluded from further analysis. In order to exclude any low quality samples, any sample with a detected number of miRNAs below 100 was removed.

Data Filtering and Normalization of Data

The amplification efficiency was calculated using algorithms similar to the LinReg software. All assays were inspected for distinct melting curves and the Tm was checked to be within known specifications for the assay. Furthermore assays must be detected with 3 Cps less than the negative control, and with Cp<37 to be included in the data analysis. Data that did not pass these criteria were omitted from any further analysis. Cp was calculated as the $2^{nd}$ derivative. In order to exclude any low quality samples, any sample with a detected number of miRNAs below 100 was removed. Using NormFinder the best normalizer was found to be the average of assays detected in all samples. All data was normalized to the average of assays detected in all samples (N=23) (average—assay Cp), a robust method shown to be the best normalization for qRT-PCR studies involving numerous assays (13). The 23 assays are: hsa-let-7a-5p, hsa-let-7b-5p, hsa-let-7f-5p, hsa-let-7g-5p, hsa-miR-10b-5p, hsa-miR-125b-5p, hsa-miR-1260a, hsa-miR-141-3p, hsa-miR-16-5p, hsa-miR-19b-3p, hsa-miR-200b-3p, hsa-miR-200c-3p, hsa-miR-204-5p, hsa-miR-23b-3p, hsa-miR-24-3p, hsa-miR-26a-5p, hsa-miR-27b-3p, hsa-miR-30a-5p, hsa-miR-30b-5p, hsa-miR-30c-5p, hsa-miR-99a-5p and hsa-miR-99b-5p.

Statistical Analysis

Expression Analysis:

For all analyses P values<0.05 were considered statistically significant. The Shapiro Wilk test was used to evaluate if data was normally distributed. As several of the microRNAs were not, a non-parametric statistic Wilcoxon signed-rank test were used for the pairwise comparisons of microRNA expression between the different groups. The diagnostic potential of miRNA expression was evaluated by Receiver Operator Characteristics (ROC) curve analysis.

Results

Expression Data:

Several microRNAs were found to be significantly regulated (P<0.01) based on Wilcoxon rank test, the top 20 being: hsa-miR-135b-5p, hsa-miR-140-3p, hsa-miR-141-3p, hsa-miR-146a-5p, hsa-miR-16-5p, hsa-miR-19a-3p, hsa-miR-200c-3p, hsa-miR-205-5p, hsa-miR-20a-5p, hsa-miR-222-3p, hsa-miR-23a-3p, hsa-miR-24-3p, hsa-miR-27b-3p, hsa-miR-30a-3p, hsa-miR-30a-5p, hsa-miR-30b-5p, hsa-miR-30c-5p, hsa-miR-30e-5p, hsa-miR-31-5p and hsa-miR-362-5p.

Diagnostic Performance of microRNA Expression and Development of a Diagnostic microRNA Classifier The diagnostic potential of a miRNA can be assessed by receiver operating characteristic (ROC), using the area under the curve (AUC) as a measure for performance. In this regard, miRNA-31-5p displays the highest potential, having an AUC of 0.92 in the discovery cohort.

To increase the detection difference and circumvent the need for normalization, thereby increasing the robustness of the assay, we calculated the ratio of the most significantly upregulated miRNAs versus the most robustly significant down regulated miRNAs. We found that the ratio between miRNA-31-5p and miR-30c gave a higher AUC value than miRNA-31-5p on its own (Table 3).

Conclusion

Despite the uneven distribution of categories with only 8 controls (BPH) against 122 cases (RP) we were able to identify the ratio of miR-31-5p vs. miR-30c as a powerful 2 miR classifier with an excellent diagnostic accuracy, as determined by area under (AUC) the ROC curve (AUC=0.92), with specificity of 85.7% and sensitivity of 92.2%.

EXAMPLE 3

Title: Validation of the Diagnostic Performance of the 2 miR (Cp(miR-31-5p)-Cp(miR-30c)) Classifier Aim To verify the miRNA expression pattern of urine samples from PC patients compared samples from controls and validate the 2 miR (Cp(miR-31-5p)-Cp(miR-30c)) classifier identified in Example 2, Specimens (Cohort 2)

All urine samples were collected at Department of Urology and obtained from Institute of Pathology, Aarhus University Hospital, Denmark (from 1997-2005). For all individuals sections of H&E stained formalin fixed paraffin embedded tissue specimens were evaluated by a trained pathologist. The validation cohort (cohort 2) consisted of 47 non-malignant samples (controls: BPH patients), 98 samples from patients with undergoing curatively intended RP for s of histologically verified clinically localized PC (RP) and 3 Castration Resistant Prostate Cancer (CRPC). See table 2 for overview of sample composition of cohorts Method Sample Preparation As example 1, MicroRNA Expression Profiling Profiling was performed exactly as in Example 2, Data Filtering and Normalization of Data Data filtering and normalization was performed exactly as in Example 2, All data was normalized to the average of assays detected in all samples (N=23) (average—assay Cp), a robust method shown to be the best normalization for qRT-PCR studies involving numerous assays (14).

Statistical Analysis

Expression Analysis:

For all analyses P values<0.05 were considered statistically significant. The Shapiro Wilk test was used to evaluate if data was normally distributed. As several of the microRNAs were not, a non-parametric statistic Wilcoxon signed-rank test were used for the pairwise comparisons of microRNA expression between the different groups. P values were corrected for multiple testing using the Benjamini-Hochberg method (15). The diagnostic potential of miRNA expression was evaluated by Receiver Operator Characteristics (ROC) curve analysis.

Results

Several microRNAs were found to be significantly regulated (P<0.01) based on Wilcoxon rank test adjusted for multiple testing (Benjamin Hochberg (BH) method), the top 20 being: hsa-miR-141-3p, hsa-miR-142-3p, hsa-miR-146a-5p, hsa-miR-151a-3p, hsa-miR-16-5p, hsa-miR-191-5p, hsa-miR-200c-3p, hsa-miR-203a, hsa-miR-204-5p, hsa-miR-205-5p, hsa-miR-222-3p, hsa-miR-223-3p, hsa-miR-24-3p, hsa-miR-30a-5p, hsa-miR-30c-5p, hsa-miR-31-3p, hsa-miR-31-5p, hsa-miR-320a, hsa-miR-93-5p and hsa-miR-99a-5p, Between these top 20 significantly regulated miRNAs there was an overlap of 10 significantly regulated miRNAs between cohort 1 and 2 (Table 3).

As seen in table 3, the miRNA with strongest diagnostic potential for discrimination between cancer and controls is miR-31-5p and miR-146, However miR-146 is only detected in 60% of samples and is thus not a suitable candidate, whereas miR-31-5p is detected in 96% of the samples (AUC=0.85)

cases and controls even in a cohorts that was sampled and processed according to a considerable different methodology. The specimens of cohort 3 differed from cohort 1 and 2 with regard to the following parameters: 1) Nationality (UK), 2) sampling (prostate massaged before sampling), 3) RNA extraction technology (extraction from whole cell free urine without enrichment for exosomes—different Kit used). Thus an overlap to example 1 and 2 of the two miRNAs being significantly up/down regulated would be proof of the robustness Specimens Urine samples were provided by Department of Oncology, The Medical School, Sheffield, UK. The validation cohort 3 consisted of 34 non-malignant control samples, 36 samples from patients with localized prostate cancer, 20 patients with advanced PC. RNA was extracted directly from the cell free urine fraction (supernatant) using the mirVana™ miRNA Isolation Kit (Catalog number:

TABLE 3

Significantly regulated miRNA in both cohort 1 and 2, MiRs are ranked according to the p-value based on Wilcoxon rank test in the validation cohort after adjustment for multiple testing by the Benjamin Hochberg (BH) method.

| | Cohort 2 (validation) | | | Cohort 1 (discovery) | | |
| --- | --- | --- | --- | --- | --- | --- |
| miRname | Fold change | BH adj. p-value | AUC (95% CI) (p < 0.0001) | Fold change | BH adj. Wilcoxon p-value | AUC (95% CI) (p > 0.0001) |
| hsa-miR-31-5p | −2.7 | 1.70E−08 | 0.85 (0.77 to 0.92) | −3.5 | 0.001298 | 0.92 (0.83 to 1.00) |
| hsa-miR-146a-5p | −8.9 | 4.70E−08 | 0.86 (0.78 to 0.94) | −13 | 9.5E−05 | 0.95 (0.89 to 1.00) |
| hsa-miR-205-5p | −2.6 | 0.000015 | 0.78 (0.69 to 0.88) | −3 | 0.007226 | 0.85 (0.66 to 1.00) |
| hsa-miR-16-5p | −1.7 | 0.000015 | 0.79 (0.70 to 0.88) | −1.6 | 0.000226 | 0.84 (0.75 to 0.95) |
| hsa-miR-200c-3p | −1.5 | 0.000031 | 0.76 (0.67 to 0.85) | −1.5 | 0.00224 | 0.82 (0.63 to 1.00) |
| hsa-miR-30c-5p | 1.3 | 0.00026 | 0.73 (0.75 to 0.81) | 1.6 | 0.002904 | 0.86 (0.71 to 1.00) |
| hsa-miR-24-3p | −1.4 | 0.00047 | 0.74 (0.64 to 0.83) | −1.4 | 7.69E−05 | 0.86 (0.77 to 0.95) |
| hsa-miR-141-3p | −1.5 | 0.00051 | 0.78 (0.69 to 0.87) | −1.6 | 0.015074 | 0.83 (0.66 to 1.00) |
| hsa-miR-222-3p | −1.6 | 0.001 | 0.74 (0.65 to 0.83) | −1.6 | 0.014024 | 0.79 (0.64 to 0.94) |
| hsa-miR-30a-5p | 1.3 | 0.0013 | 0.71 (0.62 to 0.81) | 1.6 | 0.001836 | 0.85 (0.75 to 0.96) |
| miR2 (miR31-5p/miR30c) | — | — | 0.86 (0.79 to 1.00) | — | — | 0.92 (0.80 to 1.00) |

"Fold change" is the relative difference in miR-expression between controls (BPH) and cases (RP),
"—" designate that the specific miR is downregulated in cancer.
"AUC" designate the area under the receiver operator characteristic curve.
"95% CI" designate the 95% confidence intervals (CI).

The diagnostic potential of the 2-miR (miR-31-5p/miR30c) classifier with the cut-off established in cohort 1, was validated in cohort 2 using ROC analysis, with a high diagnostic accuracy; defined by the area under the ROC curve, of 0.86 (95% CI: 0.79 to 1.00, p<0.0001) and a sensitivity of 72.5% and specificity of 84.1% was found.

Conclusion:

The diagnostic potential of miR-31-5p (normalized) and the 2 miRNA (ratio) classifier (miR-31-5p/miR-30c) were successfully validated in an independent validation cohort using a similar cut-off value as established in cohort 1, The accuracy of the diagnostic 2 miRNA (miR-31-5p/miR-30c) classifier was high (AUC=0.86), with a sensitivity and specificity of 72.5% and 84.1%, respectively.

EXAMPLE 4

Title: Test of Classifier Robustness in an Independent Cohort 3
Aim as Marker.

To test the robustness of the 2-miR classifier; i.e. its diagnostic potential to separate samples correctly into cancer AM1560) from Ambion, Life Technology, in accordance to manufacture instructions. The purified RNA was stored at −80° C. until use.

Methods

Profiling was performed as in example 3, For cohort 3, relative microRNA levels were analyzed using microRNA Ready-to-Use PCR, custom made Pick-&-Mix microRNA PCR Panel consisting of 48 selected microRNA assays and 4 spike-in controls. Samples where less than 50% of the 48 miRNAs measured were removed from sample set. Normalization of cohort 3 was performed using the NormFinder algorithm (40) on both the cohort 1 and the cohort 3, and selecting the most stably expressed miRNA in both sets as normalizing gene, hsa-miR-103a-3p.

Results

The 2 miR classifier (miR31-5p, 30c) classified cases from controls with a sensitivity and specificity of 72.9% and 84.4%, respectively, using a the cut-off value established in cohort 1 and with an area under the ROC curve of 0.79 (CI: 0.69 to 0.90, p<<0.0001), see tab 4 and FIG. 1c.

TABLE 4

Receiver operator curves were plotted for the miR-31-5p/miR-30c classifier in three cohorts see FIG. 1a, b and c, and the Area under the receiver operator characteristic curve is calculated. The 95% confidence intervals (CI) are indicated in table.

| miR classifier | Discovery (cohort 1) | | Validation (cohort 2) | | Validation (cohort 3) | |
|---|---|---|---|---|---|---|
| | AUC | 95% CI[b] | AUC | 95% CI[b] | AUC | 95% CI[b] |
| miR-31-5p/miR-30c | 0.92 | 0.80 to 1.00 | 0.86 | 0.79 to 0.100 | 0.79 | 0.69 to 0.90 |

Conclusion

Despite that cohort 3 is fundamentally different from cohort 1 and 2; difference of specimen collection, processing and normalization strategy, the diagnostic potential of miR31 was confirmed. The 2 miR classifier was successfully validated in this independent cohort (cohort 3) using the same cut-off value as established in cohort 1 and 2, The diagnostic classifier accuracy was high (AUC=0.79), with a sensitivity of 72.9% and specificity of 84.8%.

EXAMPLE 5

Title: Improved Discovery of Classifier-Based miRNA Biomarkers with Diagnostic Potential Aim It may be advantageous to use a panel of miRNAs, a classifier that does not rise or fall on the expression level of a single miRNA. To increase the statistical power of the identification of miRNA with diagnostic potential we merge cohort 1 and cohort 2 to one large discovery cohort. The merged data set has sufficient power for statistical approach for building of classifiers.

Specimens (Cohort 1 and Cohort 2)

The merged cohort (cohort 1, example 1 and cohort 2, example 2) consisted of 48 non-malignant samples (NM; from BPH patients (controls), 205 samples from patients with curatively intended RPs of histologically verified clinically localized PC and 8 Castration Resistant Prostate Cancer (CRPC).

Methods

Data Filtering and Normalization

To reduce the number of normalizers, background filtered data (where a measurement is obtained in all samples) was parsed to the Normfinder algorithm the (14). The top 5 most stable miRNAs from Normfinder (hsa-miR-20a-5p, hsa-miR-30b-5p, hsa-let-7a-5p, hsa-miR-27b-3p, hsa-miR-23b-3p) was used to calculate a mean normalization value for each sample. The mean normalization value for each individual sample is subtracted from the raw data Cp values for each individual sample in order to obtain the $\Delta$Cp value. The two normalization strategies (Top 5 miRNA and global mean normalization) gave very similar results in terms of top differentially expressed microRNAs as well as in the overall ranking of microRNAs, thus supporting the validity of the 5 microRNA as normalization genes in a subsequent validation study. The 5 miR normalization method is used for all subsequent analysis.

Construction of Classifiers

Each miRNA classifier were constructed by Monte Carlo sampling, drawing from 2 to 20 miRNAs at random from the top 100 of the most significant miRNAs between two groups (based on a Benjamini-Hochberg adjusted Wilcoxon test p-value) (17). This was done 1 million times, and each classifier was tested for performance, using ROC AUC or log-rank test p-value as score for diagnostic and prognostic classifiers, respectively. The classifier was then reduced by leave-one-out cross-validation (LOOCV) maximum likelihood classifier approaches to reduce the classifier (18).

Scoring Using the Classifier

The patient score based on a classifier was calculated as following: A cutoff value ($\Delta$Cp value) was selected for a given miRNA based on the best threshold (Youden's J statistic (Youden, 1950)) (17) from a ROC curve as determined by the pROC package in R. Then, for each patient the $\Delta$Cp value for the given miRNA was examined and if the patient $\Delta$Cp value were greater than the cutoff, the miRNA given a score of +1 or −1 if $\Delta$Cp value were less than the cutoff. Depending on whether the miRNA was up- or down-regulated the operational signs were changed accordingly. Finally, if a given miRNA was not found to be expressed within the detection limits, it was assigned a score of 0, This procedure was done for each miRNA and the results were summed in order to give a total classifier score for each patient.

Results

The top 20 miRNA found to be significantly de-regulated between BPH and RP after adjusting for multiple testing by Benjamin Hochberg in this large merged sample set are shown in table 5, 15 of the 20 miRNAs that were validated in example 3 are all contained with this set. Table 6 show all significantly de-regulated miRNAs between BPH and RP found in example 5,

TABLE 5

Top 20 miRNA with significant regulated miRNA between controls (BPH) and cases (RP).

| miRNA name | Expressed | $\Delta\Delta$Cq | Fold | Wilcox test BH | AUC |
|---|---|---|---|---|---|
| hsa-miR-31-5p | 99 | −1.77 | −3.41 | 5.3E−14 | 0.89 |
| hsa-miR-141-3p | 100 | −0.82 | −1.76 | 8.3E−12 | 0.85 |
| hsa-miR-146a-5p | 70 | −3.23 | −9.40 | 3.8E−10 | 0.88 |
| hsa-miR-222-3p | 100 | −0.83 | −1.78 | 2.8E−09 | 0.81 |
| hsa-miR-24-3p | 100 | −0.59 | −1.51 | 1.4E−08 | 0.80 |
| hsa-miR-320a | 100 | −0.74 | −1.67 | 3.9E−08 | 0.79 |
| hsa-miR-16-5p | 100 | −0.71 | −1.64 | 1.2E−07 | 0.78 |
| hsa-miR-31-3p | 89 | −1.20 | −2.30 | 1.2E−07 | 0.79 |
| hsa-miR-205-5p | 100 | −1.36 | −2.58 | 1.4E−07 | 0.78 |
| hsa-miR-200b-3p | 100 | −0.58 | −1.49 | 1.4E−07 | 0.78 |
| hsa-miR-200c-3p | 100 | −0.56 | −1.47 | 2.3E−07 | 0.77 |
| hsa-miR-203a | 100 | −0.89 | −1.86 | 2.5E−07 | 0.77 |
| hsa-miR-30c-5p | 100 | 0.39 | 1.31 | 2.5E−07 | 0.77 |
| hsa-miR-10b-5p | 100 | 0.52 | 1.43 | 9.4E−07 | 0.76 |
| hsa-miR-23b-3p | 100 | −0.27 | −1.21 | 2.0E−06 | 0.75 |
| hsa-miR-30a-5p | 100 | 0.44 | 1.36 | 3.5E−06 | 0.75 |
| hsa-miR-151a-3p | 95 | −0.80 | −1.74 | 3.6E−06 | 0.75 |

TABLE 5-continued

Top 20 miRNA with significant regulated miRNA between controls (BPH) and cases (RP).

| miRNA name | Expressed | ΔΔCq | Fold | Wilcox test BH | AUC |
|---|---|---|---|---|---|
| hsa-miR-30b-5p | 100 | 0.25 | 1.19 | 6.5E−06 | 0.74 |
| hsa-miR-378a-3p | 96 | −0.80 | −1.75 | 2.2E−05 | 0.73 |
| hsa-miR-191-5p | 100 | — | −1.45 | 5.5E−05 | 0.72 |

"ΔΔCq" is a measure of the relative difference in gene expression between controls (BPH) and cases (RP) determined by the 2-ΔΔCt method, see (20).
"Fold" is the relative difference in genexpression between controls (BPH) and cases (RP),
"—" designate that the miR is downregulated in cancer.
"Expressed" indicate the percentage of samples which express measurable amounts of the miR.

TABLE 6

Significantly de-regulated miRNAs between BPH and RP. MiRs are ranked according to the product of AUC and Expression

| miRNA name | Expressed | ΔΔCp | Fold | Wilcox test BH adjusted | AUC | Ex* AUC |
|---|---|---|---|---|---|---|
| hsa-miR-31-5p | 99 | −1.77 | −3.41 | 5.30E−14 | 0.89 | 88.11 |
| hsa-miR-141-3p | 100 | −0.82 | −1.76 | 8.30E−12 | 0.85 | 85 |
| hsa-miR-222-3p | 100 | −0.83 | −1.78 | 2.80E−09 | 0.81 | 81 |
| hsa-miR-24-3p | 100 | −0.59 | −1.51 | 1.40E−08 | 0.8 | 80 |
| hsa-miR-320a | 100 | −0.74 | −1.67 | 3.90E−08 | 0.79 | 79 |
| hsa-miR-16-5p | 100 | −0.71 | −1.64 | 1.20E−07 | 0.78 | 78 |
| hsa-miR-205-5p | 100 | −1.36 | −2.58 | 1.40E−07 | 0.78 | 78 |
| hsa-miR-200b-3p | 100 | −0.58 | −1.49 | 1.40E−07 | 0.78 | 78 |
| hsa-miR-200c-3p | 100 | −0.56 | −1.47 | 2.30E−07 | 0.77 | 77 |
| hsa-miR-203a | 100 | −0.89 | −1.86 | 2.50E−07 | 0.77 | 77 |
| hsa-miR-30c-5p | 100 | 0.39 | 1.31 | 2.50E−07 | 0.77 | 77 |
| hsa-miR-10b-5p | 100 | 0.52 | 1.43 | 9.40E−07 | 0.76 | 76 |
| hsa-miR-23b-3p | 100 | −0.27 | −1.21 | 2.00E−06 | 0.75 | 75 |
| hsa-miR-30a-5p | 100 | 0.44 | 1.36 | 3.50E−06 | 0.75 | 75 |
| hsa-miR-30b-5p | 100 | 0.25 | 1.19 | 6.50E−06 | 0.74 | 74 |
| hsa-miR-191-5p | 100 | −0.54 | −1.45 | 5.50E−05 | 0.72 | 72 |
| hsa-miR-151a-3p | 95 | −0.8 | −1.74 | 3.60E−06 | 0.75 | 71.25 |
| hsa-miR-31-3p | 89 | −1.2 | −2.3 | 1.20E−07 | 0.79 | 70.31 |
| hsa-miR-378a-3p | 96 | −0.8 | −1.75 | 2.20E−05 | 0.73 | 70.08 |
| hsa-miR-29c-3p | 100 | 0.54 | 1.45 | 2.30E−04 | 0.7 | 70 |
| hsa-miR-151a-5p | 100 | −0.38 | −1.3 | 2.50E−04 | 0.7 | 70 |
| hsa-miR-148a-3p | 98 | 0.8 | 1.74 | 2.00E−04 | 0.71 | 69.58 |
| hsa-miR-200a-3p | 100 | −0.33 | −1.26 | 5.70E−04 | 0.69 | 69 |
| hsa-miR-204-5p | 100 | 0.48 | 1.39 | 6.10E−04 | 0.69 | 69 |
| hsa-miR-125b-5p | 100 | 0.4 | 1.32 | 7.00E−04 | 0.68 | 68 |
| hsa-miR-93-5p | 100 | −0.46 | −1.38 | 8.50E−04 | 0.68 | 68 |
| hsa-miR-10a-5p | 100 | 0.67 | 1.59 | 1.10E−03 | 0.68 | 68 |
| hsa-miR-29a-3p | 98 | 0.53 | 1.44 | 4.80E−04 | 0.69 | 67.62 |
| hsa-miR-362-3p | 94 | 0.64 | 1.56 | 3.00E−04 | 0.71 | 66.74 |
| hsa-miR-30a-3p | 100 | 0.4 | 1.32 | 5.40E−03 | 0.66 | 66 |
| hsa-miR-363-3p | 98 | 0.63 | 1.55 | 2.10E−03 | 0.67 | 65.66 |
| hsa-miR-135b-5p | 99 | −0.53 | −1.45 | 3.80E−03 | 0.66 | 65.34 |
| hsa-miR-99a-5p | 100 | 0.34 | 1.26 | 5.40E−03 | 0.65 | 65 |
| hsa-miR-135a-5p | 97 | 0.76 | 1.7 | 2.20E−03 | 0.67 | 64.99 |
| hsa-miR-375 | 97 | 1.15 | 2.21 | 2.50E−03 | 0.67 | 64.99 |
| hsa-miR-331-5p | 94 | −0.64 | −1.56 | 6.30E−04 | 0.69 | 64.86 |
| hsa-miR-490-3p | 98 | 1.04 | 2.06 | 3.60E−03 | 0.66 | 64.68 |
| hsa-let-7b-5p | 100 | −0.32 | −1.25 | 1.30E−02 | 0.64 | 64 |
| hsa-miR-29b-3p | 100 | 0.38 | 1.3 | 1.70E−02 | 0.64 | 64 |
| hsa-miR-320c | 90 | −0.87 | −1.83 | 2.00E−04 | 0.71 | 63.9 |
| hsa-miR-106a-5p | 100 | 0.32 | 1.24 | 1.80E−02 | 0.63 | 63 |
| hsa-let-7c-5p | 100 | 0.27 | 1.21 | 2.40E−02 | 0.63 | 63 |
| hsa-miR-25-3p | 95 | −0.46 | −1.38 | 5.30E−03 | 0.66 | 62.7 |
| hsa-miR-425-3p | 88 | −0.66 | −1.58 | 3.70E−04 | 0.71 | 62.48 |
| hsa-miR-320b | 96 | −0.5 | −1.41 | 6.70E−03 | 0.65 | 62.4 |
| hsa-miR-146a-5p | 70 | −3.23 | −9.4 | 3.80E−10 | 0.88 | 61.6 |
| hsa-miR-660-5p | 99 | 0.38 | 1.3 | 4.50E−02 | 0.62 | 61.38 |
| hsa-miR-100-5p | 94 | 0.53 | 1.44 | 1.20E−02 | 0.65 | 61.1 |
| hsa-miR-140-3p | 86 | −0.58 | −1.49 | 3.60E−04 | 0.7 | 60.2 |
| hsa-miR-15b-5p | 95 | −0.42 | −1.34 | 4.80E−03 | 0.62 | 58.9 |
| hsa-miR-210-3p | 86 | −0.6 | −1.51 | 2.00E−02 | 0.64 | 55.04 |
| hsa-miR-130a-3p | 78 | 0.78 | 1.71 | 5.00E−03 | 0.69 | 53.82 |
| hsa-miR-200b-5p | 85 | −0.38 | −1.3 | 3.40E−02 | 0.63 | 53.55 |
| hsa-miR-223-3p | 63 | −3.81 | −14 | 1.30E−07 | 0.83 | 52.29 |
| hsa-miR-1972 | 56 | −2.45 | −5.45 | 6.00E−04 | 0.74 | 41.44 |
| hsa-miR-142-3p | 49 | −3.48 | −11.19 | 3.90E−07 | 0.83 | 40.67 |
| hsa-miR-132-3p | 47 | −0.81 | −1.76 | 4.70E−03 | 0.72 | 33.84 |
| hsa-miR-425-3p | 50 | −0.71 | −1.64 | 3.20E−02 | 0.66 | 33 |

In the combined set analyzed in example 5 the 2 miR classifier (miR-31-5p/miR-30c) showed a diagnostic accuracy based on ROC curve analysis of 0.9 (AUC).

While a single miRNA, or a ratio-based biomarker can perform well, it may increase the robustness of the classifier to use a panel of miRNAs.

Using Monte Carlo simulation, a 20-miRNA diagnostic classifier was constructed as explained above, resulting in a ROC curve as seen in FIG. 2, The analysis showed an AUC=0.99 with a specificity of 95.5% and a sensitivity of 93.6%. The 20 miRNA classifier consisted of: hsa-miR-132-3p, hsa-miR-135b-5p, hsa-miR-187-3p, hsa-miR-194-5p, hsa-miR-222-3p, hsa-miR-24-3p, hsa-miR-363-3p, hsa-miR-495-3p, hsa-miR-548c-5p, hsa-miR-96-5p, hsa-miR-135a-5p, hsa-miR-140-3p, hsa-miR-141-3p, hsa-miR-221-3p, hsa-miR-490-3p, hsa-miR-148a-3p, hsa-miR-16-5p, hsa-miR-20a-3p, hsa-miR-31-5p, hsa-miR-320a.

Ratio-Based Biomarkers

The diagnostic potential of a miRNA can be assessed by receiver operating characteristic (ROC), using the area under the curve (AUC) as a measure for performance. In this regard, miRNA-31-5p displays the highest potential, having an AUC of 89.9% in the discovery cohort.

Potentially, several miRNAs may supplement each other in a diagnostic test, thereby performing better than either single miRNA would. By calculating the ratio between miRNA-31-5p and the other miRNAs in the cohort, it was discovered that 12 other miRNAs gave a higher AUC score when combined with miRNA-31-5p than on their own (see table 7).

As seen in table 7 the best performing ratio judged on the AUC of the ROC curve is $$\frac{miR31}{mlR1238}.$$

However, hsa-miR-1238-3p is only expressed in 3% of the samples, and consequently of little practical value. If the ratios instead are ranked according to the product of AUC and Expression the ratio $$\frac{miR31}{miR30c}$$

appears to be the highest ranking ratio-based biomarker followed by $$\frac{miR10b}{miR30c}, \frac{miR29c}{miR30c}, \frac{let7a}{miR30c}$$

etc.

TABLE 7

List of miRNAs that performs well together with miRNA-31-5p. "Expressed" is a measure for in how many percentages of samples the given miRNA is found to be expressed. MiRs are ranked according to the product of AUC and Expression.

| miRNA | AUC (a) | Expressed % (E) | a × E |
|---|---|---|---|
| hsa-miR-30c-5p | 0.899 | 100 | 89.9 |
| hsa-miR-10b-5p | 0.896 | 100 | 89.6 |
| hsa-miR-29c-3p | 0.895 | 100 | 89.5 |
| hsa-let-7a-5p | 0.894 | 100 | 89.4 |
| hsa-miR-30a-5p | 0.893 | 100 | 89.3 |
| hsa-let-7e-5p | 0.888 | 100 | 88.8 |
| hsa-miR-29a-3p | 0.896 | 98 | 87.808 |
| hsa-miR-455-3p | 0.891 | 82 | 73.062 |
| hsa-miR-130a-3p | 0.894 | 78 | 69.732 |
| hsa-miR-22-5p | 0.9 | 43 | 38.7 |
| hsa-miR-136-5p | 0.939 | 20 | 18.78 |
| hsa-miR-1238-3p | 1 | 3 | 3 |

Conclusion

This example presented a different approach for discovering miRNAs with potential of discriminating between samples from controls and patients with localized prostate cancer (RP patients). The analysis revealed a list of 20 miRNAs wherein 5 of the miRNAs discovered and validated in example 2 and 3, The miRNA with highest impact on the diagnostic score were miR-320 and miR-31-5p, followed by miR 16-5p.

EXAMPLE 6

Title: Specificity for Prostate Cancer
Aim:
To verify that the identified signatures are specific for prostate cancer.
Specimens
A set of urine samples from 25 bladder-cancer patients and 8 non-bladder-cancer control individuals—sampled and processed according to the same protocol applied in examples 1, 2 and 3,
Methods
Methods used are identical to the methods used in example 1, 2 and 3,
Results
Among the top 20 ranking microRNAs with significant aberrant expression in bladder cancers vs. controls, only three microRNAs overlapped with those identified in PC, being: hsa-miR-16-5p, hsa-miR-320a and hsa-miR-10b-5p. The ROC plot for the strong PC diagnostic 2-miR classifier (miR-31-5p, miR-30c) is shown in FIG. 3 for Bladder cancer vs. Controls, showing very low discriminating value.

EXAMPLE 7

Title: The UniRT Method
Aim:
In this example the UniRT method for amplification and quantification of small non-coding RNA molecules by use of quantitative reverse transcription polymerase chain reaction (qRT-PCR) technology is described in brief. Further description is seen in EP2391736,
In brief, see FIG. 4, the UniRT protocol is a two-step protocol. In STEP 1 the miRs present in a sample are firstly poly-A-tailed using a poly(A) polymerase, which adds adenine residues to the 3'-end of RNA molecules. Secondly, an extension primer, which has a poly-T-core nucleotide sequence, a 3'-end VN-degenerate motif and a 5'-end tail, is annealed to the poly-A-tailed miRs through hybridization with the VN-poly-T-sequence of the extension primer. Subsequently, the extension primer is extended in a reverse transcription reaction using the miR as template. The resulting primary extension product is composed of the extension primer and the newly synthesized cDNA, which complementary to the miRs in the sample.

In the next step, STEP 2, a miR-specific PCR is carried out. A miR-specific forward primer is annealed to 3'-end of the newly synthesized cDNA and the upper-strand synthesis is carried out by extending the forward primer in a DNA-polymerization reaction using the primary extension product as template. A miR-specific reverse primer composed of a miR-specific 3'-end sequence, a poly-T-stretch and a 5'-end tail is then hybridized to the upper-strand and the lower-strand is synthesized by extension of the reverse primer.

In both STEP 1 and STEP 2 the LNA's help to ensure a specific and efficient annealing of the primers to their respective targets.

The UniRT method of Exiqon (miRCURY LNA™ Universal RT microRNA PCR) provide results with unmatched sensitivity and specificity, see Mestdagh et al. Nat Methods. 2014 August; 11(8):809-15,

EXAMPLE 8

Title: Improved Discovery of microRNA Classifiers in Exosome Fractionated Cell Free Urine
Aim of Study
To identify microRNA with diagnostic ability to discriminate between benign and cancer conditions.
Specimens
All urine samples were collected at Department of Urology and obtained from Institute of Pathology, Aarhus University Hospital, Denmark (from 1997-2005). For all individuals sections of H&E stained formalin fixed paraffin embedded tissue specimens were evaluated by a trained pathologist. The training cohort (cohort 4-(V)) consisted of 22 non-malignant samples (NM; from BPH patients (controls), 200 samples from patients with curatively intended RPs of histologically verified clinically localized PCa.
See table 8 and FIG. 10 for overview of cohort composition.

TABLE 8

| | Cohort | | | | | |
|---|---|---|---|---|---|---|
| | 1 | 2 | 1 + 2 merged discovery | 3 "Sheffield" | 4 Example 8 discovery | 5 "New" validate |
| BPH (non-malign) | 8 | 47 | 48 | 34 | 22 | 22 |
| CRPC | 5 | 3 | 5 | | | |
| RP | 122 | 98 | 205 | 20 | 200 | 205 |
| RP + postEndo | 1 | 0 | 1 | | | |

Method
Sample preparation and MicroRNA expression profiling was performed as described in Example 1,
Data Filtering and Normalization
MicroRNAs for which all Cq values exceeded 37 in all samples were excluded from further analysis. In order to exclude any low quality samples, any sample where the total number of expressed miRNAs falls below 50% of the potential maximum was removed. To select only robustly expressed assays, microRNA assays that are expressed in less than 80% of the samples were removed and assay with an average Cq value above 35 was removed as well.

Normalization of cohort 4 was performed by calculating a mean normalization value of the top three most stably expressed assays identified by the NormFinder algorithm (40): hsa-miR-200b-3p, hsa-miR-27b-3p, hsa-miR-30b-5p.

Classifier Building—Multiple Logistic Regressions

Given two categories (benign and cancer), it is possible to use logistic regression to model the probability that a given patient belongs to a particular category. By using multiple logistic regression model we can include more than one predictor (microRNA assay measurement).

The probability (p (X)) that a characteristic is present given the values of explanatory variables, in this case a single categorical variable (p (X)=(Y=1|X=x), i.e the probability that the patient has cancer given the estimated Cq value, can be expressed by the following model:

$$p(X) = \frac{e^{\beta_0+\beta_1 X_1+\ldots+\beta_p X_p}}{1+e^{\beta_0+\beta_1 X_1+\ldots+\beta_p X_p}}$$

Where $X=(X_1, \ldots, X_p)$ are a set of explanatory variables, in this case the $\Delta Cq$ values for a particular microRNA assay, and $\beta_0, \ldots, \beta_p$ are the coefficients. The microRNA assays were selected by LASSO (Least Absolute Shrinkage and Selection Operator) regression and coefficients are estimated by the maximum likelihood method.

Selection of microRNA Panels

Lasso regression was used as the statistical method to identify microRNA panels with optimal diagnostic potential. In order to select from microRNA with a sufficient signal to noise ratio, only miRNAs displaying at least 1.75-fold change in the discovery set between normal and PCa subjects were included. As logistic regression requires a complete dataset, multiple imputation technique was used to fill in missing values. The imputation was done using the R package "mice".

Then lasso regression was performed by using the R package glmnet to find which predictors to use. In brief, Lasso regression introduces a penalty ($\lambda$) which shrinks the coefficients to zero when $\lambda$ is increased. The more a predictor (a microRNA assay) contributes to the model, the greater the $\lambda$-value has to be before its $\beta$ becomes zero (See http://www-bcf.usc.edu/~gareth/ISL/ page 219 for a full explanation of lasso regression). The coefficients were shrunk as a result of increasing $\lambda$ and the deviance in a cross validation using cv.glmnet, indicated that using 3 or 7 predictors (microRNAs) appeared to be optimal.

The diagnostic potential of microRNA panels were assessed by ROC analyses using the p-value from the logistic regression model.

Results

The top 10 ranked microRNAs is shown in table 9, The LASSO regression indicated that using 3 or 7 predictors (microRNAs) appeared to be optimal.

TABLE 9a

Rank of microRNA and list of identified panels (based on Lasso regression). The classifiers were shrunk from 10 microRNAs (miR10) to one microRNA (miR1). The 'x' indicates that the microRNA is included in the given miR biomarker panel. i.e. panel miR3 is hsa-miR-31-5p, hsa-miR-141-3p, and hsa-miR-24-3p

| | | biomarker panels | | | | | | | | | |
|---|---|---|---|---|---|---|---|---|---|---|---|
| RANK | Assay | miR1 | miR2 | miR3 | miR4 | miR5 | miR6 | miR7 | miR8 | miR9 | miR10 |
| 1 | hsa-miR-31-5p | X | X | X | X | X | X | X | X | X | X |
| 2 | hsa-miR-141-3p | | X | X | X | X | X | X | X | X | X |
| 3 | hsa-miR-24-3p | | | X | X | X | X | X | X | X | X |
| 4 | hsa-miR-31-3p | | | | X | X | X | X | X | X | X |
| 5 | hsa-miR-16-5p | | | | | X | X | X | X | X | X |
| 6 | hsa-miR-222-3p | | | | | | X | X | X | X | X |
| 7 | hsa-miR-331-3p | | | | | | | X | X | X | X |
| 8 | hsa-miR-375 | | | | | | | | X | X | X |
| 9 | hsa-miR-378a-3p | | | | | | | | | X | X |
| 10 | hsa-miR-205-5p | | | | | | | | | | X |

TABLE 9b

Diagnostic accuracy of the biomarker panels (miR1-miR10) given by AUC values; the area under the Receiver Operator Curve (ROC) in the discovery/training set, the full validation set and the intended use sub. population.

| miR panel | Assays included | Full data | | PSA <= 10 |
|---|---|---|---|---|
| | | discovery | Validation | validation |
| 1 | hsa-miR-31-5p | 0.917 | 0.805 | 0.820 |
| 2 | hsa-miR-31-5p, hsa-miR-141-3p | 0.934 | 0.836 | 0.854 |
| 3 | hsa-miR-31-5p, hsa-miR-141-3p, hsa-miR-24-3p | 0.951 | 0.861 | 0.880 |
| 4 | hsa-miR-31-5p, hsa-miR-141-3p, hsa-miR-24-3p, hsa-miR-31-3p | 0.951 | 0.862 | 0.880 |
| 5 | hsa-miR-31-5p, hsa-miR-141-3p, hsa-miR-24-3p, hsa-miR-31-3p, hsa-miR-16-5p | 0.951 | 0.847 | 0.863 |
| 6 | hsa-miR-31-5p, hsa-miR-141-3p, hsa-miR-24-3p, hsa-miR-31-3p, hsa-miR-16-5p, hsa-miR-222-3p | 0.958 | 0.860 | 0.873 |

TABLE 9b-continued

Diagnostic accuracy of the biomarker panels (miR1-miR10) given by AUC values;
the area under the Receiver Operator Curve (ROC) in the discovery/training set,
the full validation set and the intended use sub. population.

| miR panel | Assays included | Full data discovery | Validation | PSA <= 10 validation |
|---|---|---|---|---|
| 7 | hsa-miR-31-5p, hsa-miR-141-3p, hsa-miR-24-3p, hsa-miR-31-3p, hsa-miR-16-5p, hsa-miR-222-3p hsa-miR-331-3p | 0.959 | 0.875 | 0.889 |
| 8 | hsa-miR-31-5p, hsa-miR-141-3p, hsa-miR-24-3p, hsa-miR-31-3p, hsa-miR-16-5p, hsa-miR-222-3p hsa-miR-331-3p, hsa-miR-375 | 0.958 | 0.872 | 0.884 |
| 9 | hsa-miR-31-5p, hsa-miR-141-3p, hsa-miR-24-3p, hsa-miR-31-3p, hsa-miR-16-5p, hsa-miR-222-3p hsa-miR-331-3p, hsa-miR-375, hsa-miR-378a-3p, | 0.960 | 0.868 | 0.882 |
| 10 | hsa-miR-31-5p, hsa-miR-141-3p, hsa-miR-24-3p, hsa-miR-31-3p, hsa-miR-16-5p, hsa-miR-222-3p hsa-miR-331-3p, hsa-miR-375, hsa-miR-378a-3p, hsa-miR-205-5p | 0.958 | 0.872 | 0.890 |

The single microRNA assays with highest diagnostic accuracy was hsa-miR-31-5p with an AUC of 0.92,
"PSA <= 10" designate that a previous standard prostate specific antigen (PSA) measurement has indicated that serum PSA level is 10 ng/mL or below in the individual patient (or subject).

The subsequent two microRNAs (Rank 2 and 3) both added significant accuracy to the classifier: hsa-miR-31-5p, hsa-miR-141-3p, hsa-miR-24-3p, reaching an AUC of 0.95 (cut-off: 0.94).

The microRNA panel with highest diagnostic accuracy was a 7 miR classifier: hsa-miR-31-5p, hsa-miR-141-3p, hsa-miR-24-3p, hsa-miR-31-3p, hsa-miR-16-5p, hsa-miR-222-3p, hsa-miR-331-3p, with an area under the ROC curve (AUC) of 0.96 (cut-off: 0.94). Adding more assays did not increase the discriminative power further.

Conclusion

We were able to identify several novel diagnostic biomarker microRNA panels that discriminated between benign and cancerous conditions with very high accuracy (AUC>0.95).

EXAMPLE 9

Title: Validation of the Diagnostic Performance of the Identified microRNA Biomarker Panels Aim To validate the diagnostic performance the 10 miR biomarker panels (also referred to as biomarker classifiers or miR signatures) that were identified in example 8, Specimens Samples were collected and handled as described in Example 8, The validation cohort consisted of 22 non-malignant samples (NM; from BPH patients (controls), 205 samples from patients with curatively intended RPs of histologically verified clinically localized PCa (table 8).

Method

MicroRNA Expression Profiling, Normalization and Data Filtering

As in example 8, except for using a different production lot of the microRNA Ready-to-Use PCR, Pick-&-Mix microRNA PCR Panel (custom made; item no 174845) with the exact same setup as in example 8, Results The diagnostic potential of the panels (or classifiers) defined in cohort 4 were validated in cohort 5 using ROC analysis. Results are shown in table 9b (see Example 8).

The single microRNA classifier (hsa-miR-31-5p) showed a diagnostic accuracy of 0.81 in the validation cohort, whereas the each of the two subsequent microRNAs (hsa-miR-141-3p and hsa-miR-24-3) added a considerable increase to the diagnostic accuracy reaching an AUC of 0.86 (see also FIG. 5). The microRNA panels with highest diagnostic accuracy in discriminating between benign and cancerous conditions in the discovery set; the 7-miR classifier was validated to an AUC of 0.88 (FIG. 6).

Conclusion

The diagnostic miR classifiers no. 1 to 10 (diagnostic miR signatures, or diagnostic biomarker panels no. 1 to 10) were successfully validated in an independent validation cohort using cut-off values established in cohort 4, Several of the microRNA panels were able to predict a positive outcome of a biopsy test with a diagnostic accuracy above 0.86, The most optimal microRNA biomarker panel was the 7-miR classifier. For a diagnostic test, low numbers of assays are preferable due to price and complexity of the diagnostic test. Thus, apart from the 7 miR classifier, the 3 miR (hsa-miR-31-5p, hsa-miR-141-3p, and hsa-miR-24-3p) and 4 miR (hsa-miR-31-5p, hsa-miR-141-3p, hsa-miR-24-3p, and hsa-miR-31-3p) classifiers are promising biomarker candidates.

EXAMPLE 10

Title: Validation of the Identified microRNA Biomarker Panel in the Intended Use Sub-Population Aim of Study The biomarker panels are intended to be used to support the clinical decision; whether or not to biopsy, in patients with a previous PSA test result in the 'grey zone area', below 10 ng/mL. The aim of the study was to validate if the identified biomarker panels could be applied to the sub population of patients with PSA levels below 10 ng/mL, and still discriminate between benign and cancerous conditions with high diagnostic accuracy.

Specimens

The cohort was a subset of the validation cohort. It consisted of 19 non-malignant samples (NM; from BPH patients (controls), and 83 samples from patients with curatively intended RPs of histologically verified clinically localized PCa with PSA levels below or equal to 10 ng/mL (table 8).

Method
MicroRNA Expression Profiling, Normalization and Data Filtering
See example 9,
Results The diagnostic potential of the classifiers defined in cohort 4 were validated in the subpopulation of (PSA<10) cohort 5 using ROC analysis. Results are shown in table 9, The single microRNA classifier (hsa-miR-31-5p) showed a diagnostic accuracy of 0.82 in the validation cohort, whereas the three microRNA (3-miR) classifier showed a considerable increase in diagnostic accuracy to an AUC of 0.88 in line with the discovery study in example 8, The 7-miR microRNA panel that showed the highest diagnostic accuracy in discriminating between normal and cancerous conditions in the discovery cohort was also found to hold the highest discriminative power in the validation cohort with an AUC of 0.89, Adding more microRNAs to the panel did not improve the biomarker panel, as was observed in the discovery cohort.

Conclusion

We have validated the diagnostic biomarker potential of several microRNA panels in an independent cohort consisting of the intended use population; patients with PSA levels below 10 ng/mL. Several of the microRNA panels were able to predict a positive outcome of a biopsy test with a diagnostic accuracy above 0.88,

EXAMPLE 11

Title: Ratio-Based Biomarkers for Diagnosis
Aim of Study

A ratio based microRNA biomarker signature would have the considerable advantage of increasing the detection difference by circumventing the need for normalization and thereby reduce the number of assays needed to obtain diagnostic accuracy. The aim of this study was to discover ratio based classifiers with diagnostic potential for discriminating between benign and cancerous conditions.

Specimens
As used in example 8 (discovery cohort)
Method
MicroRNA Expression Profiling and Data Filtering
Data from Example 8—no normalization.
Classifier Building—Ratio Classifiers In brief, all possible miRNA pairs from the pool of 92 were created (n=4186). Pairs that were not expressed in at least 95% of all samples were then removed and AUC was calculated for the ratio between the remaining pairs (n=823). From the top 10 microRNA ratio pairs, all possible 3-miR ratios were created.

Results

The only 3-miR ratio based classifiers that added diagnostic power above the 2-miR ratio based classifiers were: hsa-miR-24-3p, hsa-miR-222-3p, hsa-miR-30a-5p and hsa-miR-24-3p, hsa-miR-222-3p, hsa-miR-30c-5p (shown in table 10), with AUC of 0.96 for both (Sensitivity and specificity >0.9, cut-off of 2 and sensitivity 88, specificity 95, cut-off >6, respectively) (FIG. 7)

The scoring algorithm for a 3-miR ratio-classifier can be expressed as:

$$\text{Score } (S) = \frac{X_1 * X_2}{(X_3)^2}$$

Where $X_1$-$X_3$ are a set of experimentally determined values (measurements) relating to the expression level of 3 different miRs. In the preferred case the Cq value for the particular microRNA assays in the classifier is used as a measure of expression level.

As the Cq values are in logarithmic scale, the score can also be written as:

$$\text{Score} = Cq_1 + Cq_2 - 2 * Cq_3$$

Where $Cq_1$-$Cq_3$ are the Cq values observed for 3 different miRs.

The selected ratio-based classifiers circumvent the need for normalization:

$$\text{Score} = \frac{\frac{X_1}{N} * \frac{X_2}{N}}{\frac{X_3}{N} * \frac{X_3}{N}} = \frac{X_1 * X_2}{(X_3)^2}$$

Where X are the Cq values for the microRNA measurement and N are the (common selected) normalization factor.

Conclusion

Two ratio based microRNA classifiers with promising diagnostic potential in prediction of positive biopsy outcome were identified.

EXAMPLE 12

Title: Validation of the 3 miR Classifiers in the Full Data Set
Aim of Study

Validation of the biomarker potential of two identified 3 miR ratio based classifiers—in an independent patient cohort.

Specimens
As in example 9 (i.e. cohort 5, table 8)
Methods
MicroRNA Expression Profiling and Data Filtering
Data from example 9—no normalization.
Results The diagnostic potential of the two 3-miR ratio based classifiers: hsa-miR-24-3p, hsa-miR-222-3p, hsa-miR-30a-5p and hsa-miR-24-3p, hsa-miR-222-3p, hsa-miR-30c-5p with the cut-off established in cohort 1 was validated in cohort 2 using ROC analysis. The diagnostic accuracy

TABLE 10

Ratio based microRNA biomarker signature

| Ratio based panels | microRNA 1 | microRNA 2 | microRNA 3 | AUC discovery | AUC validation Full data set | AUC Validation PSA <10 |
|---|---|---|---|---|---|---|
| 3miR_1 | hsa-miR-24-3p | hsa-miR-222-3p | hsa-miR-30a-5p | 0.956 | 0.870 | 0.878 |
| 3miR_2 | hsa-miR-24-3p | hsa-miR-222-3p | hsa-miR-30c-5p | 0.955 | 0.892 | 0.907 | defined by the area under the ROC curve for the two classifiers were 0.87 (sensitivity 0.89, specificity 0.76, cut-off >2) and 0.89 (Sensitivity 0.78, specificity 0.95, cut-off >6), respectively (FIG. 8).

When the diagnostic score S is calculated as:

$$S=C(\text{hsa-miR-24-3p})+C(\text{hsa-miR-222-3p})-(2\times C(\text{hsa-miR-30a-5p})),$$

we observe that:
Accepting 1% false negatives, then a diagnostic Score (S)>0.5 would suggest that the patient should be referred to biopsy.
Accepting 2% false negatives, then an S>0.9 would suggest that the patient should be referred to biopsy. And
Accepting 5% false negatives, then a S>1.8 would suggest that the patient should be referred to biopsy.

Similarly, when the diagnostic score S is calculated as $$S=C(\text{hsa-miR-24-3p})+C(\text{hsa-miR-222-3p})-(2\times C(\text{hsa-miR-30c-5p})),$$

we observe that:
Accepting 1% false negatives, then a diagnostic Score (S)>5 would suggest that the patient should be referred to biopsy.
Accepting 2% false negatives, then an S>5.1 would suggest that the patient should be referred to biopsy. And
Accepting 5% false negatives, then a S>5.8 would suggest that the patient should be referred to biopsy.

Conclusion:
The diagnostic potential of the two identified ratio based microRNA classifiers were successfully validated in an independent validation cohort using a similar cut-off value as established in the discovery cohort. The accuracy of the diagnostic 3 miR classifiers was high with AUC of more than 0.87.

We further conclude that a diagnostic score S may be calculated for both 3 miR classifiers and used to decide on the further treatment of the patient.

EXAMPLE 13

Title: Validation of the Ratio Based Classifiers in the Intended Use Sub-Population
Aim of Study
The aim of the study is to validate if the identified ratio based classifiers can be applied to intended use sub population; patients with PSA levels similar to or below 10 ng/mL, and still discriminate between benign and cancerous subjects with high diagnostic accuracy.
Specimens
Data from cohort 5
Methods
MicroRNA Expression Profiling and Data Filtering
As in Example 9—no normalization.
Results
The 3 miR classifiers (hsa-miR-24-3p, hsa-miR-222-3p, hsa-miR-30a-5p and hsa-miR-30a-5p and hsa-miR-24-3p, hsa-miR-222-3p, hsa-miR-30c-5p) were validated in the sub-population (PSA 10 ng/mL) with a diagnostic accuracy (AUC) of 0.88 (sensitivity 0.79, specificity 0.88) and 0.91 (sensitivity 0.88, specificity 0.95), respectively (FIG. 9).

When the diagnostic score, S for a patient with PSA 10 ng/mL is calculated as:

$$S=C(\text{hsa-miR-24-3p})+C(\text{hsa-miR-222-3p})-(2\times C(\text{hsa-miR-30a-5p})),$$

we observe that:
Accepting 1% false negatives, then a diagnostic Score (S)>0.7 would suggest that the patient should be referred to biopsy.
Accepting 2% false negatives, then an S>1.5 would suggest that the patient should be referred to biopsy. And
Accepting 5% false negatives, then a S>2 would suggest that the patient should be referred to biopsy.

Similarly, when the diagnostic score S is calculated as $$S=C(\text{hsa-miR-24-3p})+C(\text{hsa-miR-222-3p})-(2\times C(\text{hsa-miR-30c-5p})),$$

we observe that:
Accepting 1% false negatives, then a diagnostic Score (S)>5 would suggest that the patient should be referred to biopsy.
Accepting 2% false negatives, then an S>5.5 would suggest that the patient should be referred to biopsy. And
Accepting 5% false negatives, then a S>6 would suggest that the patient should be referred to biopsy.

Conclusion
The diagnostic biomarker potential of the two 3 miR ratio based classifiers was successfully validated in the intended use sub-population (PSA 10 ng/mL) of cohort 2 with high diagnostic accuracy of 0.88 and 0.91, respectively. The diagnostic cut-off values to be applied on clinical samples would be between 0.5 and 2 (dynamic range: [−3, +6] for the first 3 miR classifier (hsa-miR-24-3p, hsa-miR-222-3p, hsa-miR-30a-5p and hsa-miR-30a-5p) and between 4 and 6.5 (dynamic range: [1.10] for the second 3 miR classifier (hsa-miR-24-3p, hsa-miR-222-3p, hsa-miR-30c-5p).

We further conclude that a diagnostic score S may be calculated for both 3 miR classifiers and used to decide on the further treatment of the patient.

EXAMPLE 14

Title: Test of Robustness of Ratio Based Classifiers in an Independent Cohort (Cohort 3 of Example 4)
Aim
To test the robustness of the two three-mir ratio-based classifiers; i.e. their diagnostic potential to separate samples correctly into benign and cancerous conditions, even in a cohort that was sampled and processed according to a fundamentally different methodology as described in example 4,
Specimens
See example 4,
Methods
See example 4,
Results
One of the 3-miR classifiers (hsa-miR-24-3p, hsa-miR-222-3p, hsa-miR-30c-5p) classified benign from cancerous conditions with an accuracy (area under the ROC curve) of 0.79 (CI: 0.68 to 0.87, p<<0.0001, sensitivity and specificity of 64% and 84%, respectively) see FIG. 11, The diagnostic potential of the other ratio based 3miR classifier (hsa-miR-24-3p, hsa-miR-222-3p, hsa-miR-30a-5p) could not be confirmed (AUC of 0.66).

Conclusion
Although not to be expected based on the fundamental differences between cohort 3 and the discovery cohort (cohort 4); difference of specimen collection and processing, the diagnostic potential of one of the ratio based classifiers was confirmed. This classifier (hsa-miR-24-3p, hsa-miR-222-3p, hsa-miR-30c-5p) was successfully validated in cohort 3 with a diagnostic accuracy (AUC) of 0.79 in discriminating between benign and cancerous conditions Tables

TABLE 11

| All miRs in miRBase ver 21 nomenclature | Seq ID No | Sequence |
|---|---|---|
| hsa-let-7a-5p | 1 | UGAGGUAGUAGGUUGUAUAGUU |
| hsa-let-7b-5p | 2 | UGAGGUAGUAGGUUGUGUGGUU |
| hsa-let-7c-5p | 3 | UGAGGUAGUAGGUUGUAUGGUU |
| hsa-let-7e-5p | 4 | UGAGGUAGGAGGUUGUAUAGUU |
| hsa-let-7f-5p | 5 | UGAGGUAGUAGAUUGUAUAGUU |
| hsa-let-7g-5p | 6 | UGAGGUAGUAGUUUGUACAGUU |
| hsa-miR-100-5p | 7 | AACCCGUAGAUCCGAACUUGUG |
| hsa-miR-106a-5p | 8 | AAAAGUGCUUACAGUGCAGGUAG |
| hsa-miR-107 | 9 | AGCAGCAUUGUACAGGGCUAUCA |
| hsa-miR-10a-5p | 10 | UACCCUGUAGAUCCGAAUUUGUG |
| hsa-miR-10b-5p | 11 | UACCCUGUAGAACCGAAUUUGUG |
| hsa-miR-1238-3p | 12 | CUUCCUCGUCUGUCUGCCCC |
| hsa-miR-125a-5p | 13 | UCCCUGAGACCCUUUAACCUGUGA |
| hsa-miR-125b-5p | 14 | UCCCUGAGACCCUAACUUGUGA |
| hsa-miR-1260a | 15 | AUCCCACCUCUGCCACCA |
| hsa-miR-130a-3p | 16 | CAGUGCAAUGUUAAAAGGGCAU |
| hsa-miR-132-3p | 17 | UAACAGUCUACAGCCAUGGUCG |
| hsa-miR-135a-5p | 18 | UAUGGCUUUUUAUUCCUAUGUGA |
| hsa-miR-135b-5p | 19 | UAUGGCUUUUCAUUCCUAUGUGA |
| hsa-miR-136-5p | 20 | ACUCCAUUUGUUUUGAUGAUGGA |
| hsa-miR-140-3p | 21 | UACCACAGGGUAGAACCACGG |
| hsa-miR-141-3p | 22 | UAACACUGUCUGGUAAAGAUGG |
| hsa-miR-142-3p | 23 | UGUAGUGUUUCCUACUUUAUGGA |
| hsa-miR-146a-5p | 24 | UGAGAACUGAAUUCCAUGGGUU |
| hsa-miR-148a-3p | 25 | UCAGUGCACUACAGAACUUUGU |
| hsa-miR-151a-3p | 26 | CUAGACUGAAGCUCCUUGAGG |
| hsa-miR-151a-5p | 27 | UCGAGGAGCUCACAGUCUAGU |
| hsa-miR-15b-5p | 28 | UAGCAGCACAUCAUGGUUUACA |
| hsa-miR-16-5p | 29 | UAGCAGCACGUAAAUAUUGGCG |
| hsa-miR-191-5p | 30 | CAACGGAAUCCCAAAAGCAGCUG |
| hsa-miR-1972 | 31 | UCAGGCCAGGCACAGUGGCUCA |
| hsa-miR-19a-3p | 32 | UG UGCAAAUCUAUGCAAAACUGA |
| hsa-miR-200a-3p | 33 | UAACACUGUCUGGUAACGAUGU |
| hsa-miR-200b-3p | 34 | UAAUACUGCCUGGUAAUGAUGA |
| hsa-miR-200b-5p | 35 | CAUCUUACUGGGCAGCAUUGGA |
| hsa-miR-200c-3p | 36 | UAAUACUGCCGGGUAAUGAUGGA |
| hsa-miR-203a-3p | 37 | GUGAAAUGUUUAGGACCACUAG |

TABLE 11-continued

| All miRs in miRBase ver 21 nomenclature | Seq ID No | Sequence |
|---|---|---|
| hsa-miR-204-5p | 38 | UUCCCUUUGUCAUCCUAUGCCU |
| hsa-miR-205-5p | 39 | UCCUUCAUUCCACCGGAGUCUG |
| hsa-miR-20a-5p | 40 | UAAAGUGCUUAUAGUGCAGGUAG |
| hsa-miR-210-3p | 41 | CUGUGCGUGUGACAGCGGCUGA |
| hsa-miR-222-3p | 42 | AGCUACAUCUGGCUACUGGGU |
| hsa-miR-223-3p | 43 | UGUCAGUUUGUCAAAUACCCCA |
| hsa-miR-22-5p | 44 | AGUUCUUCAGUGGCAAGCUUUA |
| hsa-miR-23a-3p | 45 | AUCACAUUGCCAGGGAUUUCC |
| hsa-miR-23b-3p | 46 | AUCACAUUGCCAGGGAUUACC |
| hsa-miR-24-3p | 47 | UGGCUCAGUUCAGCAGGAACAG |
| hsa-miR-25-3p | 48 | CAUUGCACUUGUCUCGGUCUGA |
| hsa-miR-26a-5p | 49 | UUCAAGUAAUCCAGGAUAGGCU |
| hsa-miR-27b-3p | 50 | UUCACAGUGGCUAAGUUCUGC |
| hsa-miR-29a-3p | 51 | UAGCACCAUCUGAAAUCGGUUA |
| hsa-miR-29b-3p | 52 | UAGCACCAUUUGAAAUCAGUGUU |
| hsa-miR-29c-3p | 53 | UAGCACCAUUUGAAAUCGGUUA |
| hsa-miR-30a-3p | 54 | CUUUCAGUCGGAUGUUUGCAGC |
| hsa-miR-30a-5p | 55 | UGUAAACAUCCUCGACUGGAAG |
| hsa-miR-30b-5p | 56 | UGUAAACAUCCUACACUCAGCU |
| hsa-miR-30c-5p | 57 | UGUAAACAUCCUACACUCUCAGC |
| hsa-miR-30e-5p | 58 | UGUAAACAUCCUUGACUGGAAG |
| hsa-miR-31-3p | 59 | UGCUAUGCCAACAUAUUGCCAU |
| hsa-miR-31-5p | 60 | AGGCAAGAUGCUGGCAUAGCU |
| hsa-miR-320a | 61 | AAAAGCUGGGUUGAGAGGGCGA |
| hsa-miR-320b | 62 | AAAAGCUGGGUUGAGAGGGCAA |
| hsa-miR-320c | 63 | AAAAGCUGGGUUGAGAGGGU |
| hsa-miR-331-3p | 64 | GCCCCUGGGCCUAUCCUAGAA |
| hsa-miR-362-3p | 65 | AACACACCUAUUCAAGGAUUCA |
| hsa-miR-362-5p | 66 | AAUCCUUGGAACCUAGGUGUGAGU |
| hsa-miR-363-3p | 67 | AAUUGCACGGUAUCCAUCUGUA |
| hsa-miR-375 | 68 | UUUGUUCGUUCGGCUCGCGUGA |
| hsa-miR-378a-3p | 69 | ACUGGACUUGGAGUCAGAAGGC |
| hsa-miR-425-3p | 70 | AUCGGGAAUGUCGUGUCCGCCC |
| hsa-miR-425-5p | 71 | AAUGACACGAUCACUCCCGUUGA |
| hsa-miR-455-3p | 72 | GCAGUCCAUGGGCAUAUACAC |
| hsa-miR-490-3p | 73 | CAACCUGGAGGACUCCAUGCUG |
| hsa-miR-660-5p | 74 | UACCCAUUGCAUAUCGGAGUUG |
| hsa-miR-92a-3p | 75 | UAUUGCACUUGUCCCGGCCUGU |

TABLE 11-continued

| All miRs in miRBase ver 21 nomenclature | Seq ID No | Sequence |
|---|---|---|
| hsa-miR-93-5p | 76 | CAAAGUGCUGUUCGUGCAGGUAG |
| hsa-miR-99a-5p | 77 | AACCCGUAGAUCCGAUCUUGUG |
| hsa-miR-99b-5p | 78 | CACCCGUAGAACCGACCUUGCG |

REFERENCES

1. Ferlay J, Soerjomataram I, Dikshit R, Eser S, Mathers C, Rebelo M, et al. Cancer incidence and mortality worldwide: Sources, methods and major patterns in GLOBO-CAN 2012, International journal of cancer Journal international du cancer. 2014.
2. Catalona (1996) The Prostate vol 29, Issue Supplement 7, p 64-69)
3. Carthew R W, Sontheimer E J. Cell. 2009; 136:642-55.
4. Zeng Y, Cullen B R. RNA. 2003; 9:112-23.
5. Gregory R I, et al. Cell. 2005; 123:631-40.
6. Kozomara A, Griffiths-Jones S. Nucleic Acids Res. 2014; 42:D68-73.
7. Friedman R C, Farh K K, Burge C B, Bartel D P. Genome research. 2009; 19:92-105.
8. Di Leva G, Garofalo M, Croce C M. Annual review of pathology. 2014; 9:287-314.
9. Bartels C L, Tsongalis G J. Clin Chem. 2009; 55:623-31.
10. Tong A W, et al. Cancer Gene Ther. 2009; 16:206-16.
11. Verma et al (2014) The Canadian Journal of Urology 21(3):7312-7321))
12. Huang et al. (2014) Am J Clin Exp Urol. 2(4): 343-350)
13. Bustin, S. A. (ed.) A-Z of quantitative PCR, IUL Biotechnology Series 5 (2004) 882 pages
14. Andersen C L, Jensen J L, Orntoft T F. Cancer Res. 2004; 64:5245-50.
15. Benjamini Y, Hochberg Y. Journal of the Royal Statistical Society. Series B (Methodological), 1995.
16. Dramiński M, Rada-Iglesias, Enroth S, Wadelius C, Koronacki, et al (2008) Bioinformatics (2008) 24 (1): 110-117.
17. Dyrskjot et al. Nature genetics. 2003; 33:90-6.
18. Youden W J. Index for rating diagnostic tests. Cancer 1950; 3:32-5.
19. Goessl (2001) Urology. 2001 September; 58(3):335-8.
20. Livak and Schmittgen (2001) METHODS 25, 402-408.
21. Tom Mitchell, Machine Learning, McGraw Hill, 1997.

The invention claimed is:

1. An in vitro method for assessing the risk that a subject suffers from prostate cancer, comprising:
   a) measuring the expression level of at least two miRs selected from group of miRs consisting of: hsa-let-7a-5p, hsa-let-7b-5p, hsa-let-7c-5p, hsa-let-7e-5p, hsa-let-7f-5p, hsa-let-7g-5p, hsa-miR-100-5p, hsa-miR-106a-5p, hsa-miR-10a-5p, hsa-miR-10b-5p, hsa-miR-1238-3p, hsa-miR-125b-5p, hsa-miR-1260a, hsa-miR-130a-3p, hsa-miR-132-3p, hsa-miR-135a-5p, hsa-miR-135b-5p, hsa-miR-136-5p, hsa-miR-140-3p, hsa-miR-141-3p, hsa-miR-142-3p, hsa-miR-146a-5p, hsa-miR-148a-3p, hsa-miR-151a-3p, hsa-miR-151a-5p, hsa-miR-15b-5p, hsa-miR-16-5p, hsa-miR-191-5p, hsa-miR-1972, hsa-miR-19a-3p, hsa-miR-19b-3p, hsa-miR-200a-3p, hsa-miR-200b-3p, hsa-miR-200b-5p, hsa-miR-200c-3p, hsa-miR-203a, hsa-miR-204-5p, hsa-miR-205-5p, hsa-miR-20a-5p, hsa-miR-210, hsa-miR-222-3p, hsa-miR-223-3p, hsa-miR-22-5p, hsa-miR-23a-3p, hsa-miR-23b-3p, hsa-miR-24-3p, hsa-miR-25-3p, hsa-miR-26a-5p, hsa-miR-27b-3p, hsa-miR-29a-3p, hsa-miR-29b-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-320b, hsa-miR-320c, hsa-miR-331-3p, hsa-miR-362-3p, hsa-miR-362-5p, hsa-miR-363-3p, hsa-miR-375, hsa-miR-378a-3p, hsa-miR-425-3p, hsa-miR-425-5p, hsa-miR-455-3p, hsa-miR-490-3p, hsa-miR-660-5p, hsa-miR-93-5p, hsa-miR-99a-5p, and hsa-miR-99b-5p in a urine sample from said subject, wherein a changed expression level of said at least 2 miRs, as compared to healthy donors, indicates an increased probability of said subject suffering from prostate cancer;
   b) calculating a diagnostic score (S) based on a dataset comprising the expression level data of said at least two miRs as a ratio vs. the expression level of hsa-miR-30a-5p, or vs. the expression level of hsa-miR-30c-5p; and
   c) treating said subject with a suitable therapy based on the diagnostic score S of said subject.

2. An in vitro method according to claim 1 wherein said at least 2 miRs are selected from the group of miRs consisting of: hsa-let-7a-5p, hsa-let-7e-5p, hsa-miR-10b-5p, hsa-miR-1238-3p, hsa-miR-130a-3p, hsa-miR-135b-5p, hsa-miR-136-5p, hsa-miR-140-3p, hsa-miR-141-3p, hsa-miR-142-3p, hsa-miR-146a-5p, hsa-miR-151a-3p, hsa-miR-16-5p, hsa-miR-191-5p, hsa-miR-19a-3p, hsa-miR-200b-3p, hsa-miR-200c-3p, hsa-miR-203a, hsa-miR-204-5p, hsa-miR-205-5p, hsa-miR-20a-5p, hsa-miR-222-3p, hsa-miR-223-3p, hsa-miR-22-5p, hsa-miR-23a-3p, hsa-miR-23b-3p, hsa-miR-24-3p, hsa-miR-27b-3p, hsa-miR-29a-3p, hsa-miR-29c-3p, hsa-miR-30a-3p, hsa-miR-30a-5p, hsa-miR-30b-5p, hsa-miR-30c-5p, hsa-miR-30e-5p, hsa-miR-31-3p, hsa-miR-31-5p, hsa-miR-320a, hsa-miR-362-5p, hsa-miR-378a-3p, hsa-miR-455-3p, hsa-miR-93-5p and hsa-miR-99a-5p.

3. The method according to claim 1, wherein the at least two miRs are selected from the group of miRs consisting of: hsa-miR-141-3p, hsa-miR-142-3p, hsa-miR-146a-5p, hsa-miR-151a-3p, hsa-miR-16-5p, hsa-miR-191-5p, hsa-miR-200c-3p, hsa-miR-203a, hsa-miR-204-5p, hsa-miR-205-5p, hsa-miR-222-3p, hsa-miR-223-3p, hsa-miR-24-3p, hsa-miR-30a-5p, hsa-miR-30c-5p, hsa-miR-31-3p, hsa-miR-31-5p, hsa-miR-320a, hsa-miR-93-5p and hsa-miR-99a-5p.

4. The method according to claim 1, wherein the at least two miRs are selected from the group of miRs consisting of: hsa-miR-141-3p, hsa-miR-146a-5p, hsa-miR-16-5p, hsa-miR-200c-3p, hsa-miR-205-5p, hsa-miR-222-3p, hsa-miR-24-3p, hsa-miR-30a-5p, hsa-miR-30c-5p and hsa-miR-31-5p.

5. The method according to claim 1, wherein the at least two miRs are selected from the group of miRs consisting of: hsa-miR-141-3p, hsa-miR-16-5p, hsa-miR-205-5p, hsa-miR-222-3p, hsa-miR-24-3p, hsa-miR-31-3p, hsa-miR-31-5p, hsa-miR-331-3p, hsa-miR-375, and hsa-miR-378a-3p.

6. The method according to claim 1, wherein the at least two miRs are selected from the group of miRs consisting of: hsa-miR-141-3p, hsa-miR-16-5p, hsa-miR-222-3p, hsa-miR-24-3p, hsa-miR-31-3p, hsa-miR-31-5p, hsa-miR-331-3p, hsa-miR-375, and hsa-miR-378a-3p.

7. The method according to claim 1, wherein the at least two miRs are selected from the group of miRs consisting of:

hsa-miR-141-3p, hsa-miR-16-5p, hsa-miR-222-3p, hsa-miR-24-3p, hsa-miR-31-3p, hsa-miR-31-5p, hsa-miR-331-3p, and hsa-miR-375.

8. The method according to claim 1, wherein the at least two miRs are selected from the group of miRs consisting of: hsa-miR-141-3p, hsa-miR-16-5p, hsa-miR-222-3p, hsa-miR-24-3p, hsa-miR-31-3p, hsa-miR-31-5p, and hsa-miR-331-3p.

9. The method according to claim 1, wherein the at least two miRs are selected from the group of miRs consisting of: hsa-miR-146a-5p, hsa-miR-16-5p, hsa-miR-200c-3p, hsa-miR-205-5p, hsa-miR-30c-5p and hsa-miR-31-5p.

10. The method according to claim 1, wherein the at least two miRs are selected from the group of miRs consisting of: hsa-miR-141-3p, hsa-miR-16-5p, hsa-miR-222-3p, hsa-miR-24-3p, hsa-miR-31-3p, and hsa-miR-31-5p.

11. The method according to claim 1, wherein the at least two miRs are selected from the group of miRs consisting of: hsa-miR-141-3p, hsa-miR-16-5p, hsa-miR-24-3p, hsa-miR-31-3p, and hsa-miR-31-5p.

12. The method according to claim 1, wherein the at least two miRs are selected from the group of miRs consisting of: hsa-miR-141-3p, hsa-miR-24-3p, hsa-miR-31-3p, and hsa-miR-31-5p.

13. The method according to claim 1, wherein the at least two miRs are selected from the group of miRs consisting of: hsa-miR-141-3p, hsa-miR-24-3p, and hsa-miR-31-5p.

14. The method according to claim 1, wherein the at least 2 miRs are 3, 4, 5 or more miRs.

15. The method according to claim 1, wherein the at least two selected miRs are: hsa-miR-30c-5p, hsa-miR-222-3p, and hsa-miR-24-3p.

16. The method according to claim 1, wherein the at least two selected miRs are: hsa-miR-30a-5p, hsa-miR-222-3p, and hsa-miR-24-3p.

17. The method according to claim 1, wherein the at least two selected miRs are hsa-miR-30c-5p and hsa-miR-31-5p.

18. The method according to claim 1, wherein expression levels are normalized expression levels.

19. The method according to claim 1, wherein expression levels are normalized expression levels, the normalization being performed by calculating a mean normalization value of 5 miRs being: hsa-miR-20a-5p, hsa-miR-30b-5p, hsa-let-7a-5p, hsa-miR-27b-3p, and hsa-miR-23b-3p.

20. The method according to claim 1, wherein expression levels are normalized expression levels, the normalization being performed by calculating a mean normalization value of 3 miRs being: hsa-miR-200b-3p, hsa-miR-27b-3p, and hsa-miR-30b-5p.

21. The method according to claim 1, wherein the expression level of said miRs is measured in an exosome preparation, prepared from said urine sample.

22. The method according to claim 1, wherein the subject having assessed the risk of prostate cancer, is characterized by a previous standard prostate specific antigen (PSA) measurement that has indicated that serum PSA level is below 10 ng/ml.

23. The method according to claim 1, wherein the urine sample is from a subject who has been subjected to prostatic massage immediately before the urine was sampled.

24. The method of claim 1, wherein the expression level of said miRs is determined by the method of quantitative polymerase chain reaction (Q-PCR).

25. The method according to claim 1, wherein the diagnostic score S is calculated as a ratio of the expression level of hsa-miR-30c-5p vs. the expression level of hsa-miR-31-5p.

26. The method according to claim 1, wherein the diagnostic score S is calculated as a ratio of the expression level of hsa-miR-24-3p and hsa-miR-222-3p vs. the expression level of hsa-miR-30a-5p.

27. The method according to claim 1, wherein the diagnostic score S is calculated as a ratio of the expression level of hsa-miR-24-3p and hsa-miR-222-3p vs. the expression level of hsa-miR-30c-5p.

28. The method according to claim 25, wherein the diagnostic score S is calculated as follows:

$$S = X^* C(\text{hsa-miR-30c-5p}) + Y^* C(\text{hsa-miR-31-5p})$$

wherein "C" is the threshold cycle value (Ct) or the crossing point value (Cp), and wherein X and Y are coefficients determined by linear regression.

29. The method according to claim 26, wherein the diagnostic score S is calculated as follows:

$$S = C(\text{hsa-miR-24-3p}) + C(\text{hsa-miR-222-3p}) - (2 \times C(\text{hsa-miR-30a-5p}))$$

wherein "C" is the threshold cycle value (Ct) or the crossing point value (Cp) obtained by quantitative real-time PCR (qRT-PCR) for hsa-miR-24-3p, hsa-miR-222-3p and hsa-miR-30a-5p, respectively.

30. The method according to claim 27, wherein the diagnostic score S is calculated as follows:

$$S = C(\text{hsa-miR-24-3p}) + C(\text{hsa-miR-222-3p}) - (2 \times C(\text{hsa-miR-30c-5p}))$$

wherein "C" is the threshold cycle value (Ct) or the crossing point value (Cp) obtained by quantitative real-time PCR (qRT-PCR) for hsa-miR-24-3p, hsa-miR-222-3p and hsa-miR-30c-5p, respectively.

31. The method according to claim 1, wherein the diagnostic score S is calculated as $$\text{Score } (S) = \frac{e^{\beta_0 + \beta_1 X_1 + \ldots + \beta_p X_p}}{1 + e^{\beta_0 + \beta_1 X_1 + \ldots + \beta_p X_p}}$$

wherein $X = (X1, \ldots, Xp)$ are the $\Delta Cq$ values for particular microRNA assays, obtained by subtracting the raw data Cq values for each individual sample from the normalization value for each individual sample, and $\beta_0, \ldots, \beta_p$ are the coefficients estimated by the maximum likelihood method.

32. The method according to claim 31, wherein the $\Delta Cq$ values are the values of the particular microRNA assays for hsa-miR-141-3p, hsa-miR-16-5p, hsa-miR-222-3p, hsa-miR-24-3p, hsa-miR-31-3p, hsa-miR-31-5p, and hsa-miR-331-3p, normalized with respect to mean Cq values of the microRNA assays for hsa-miR-200b-3p, hsa-miR-27b-3p, and hsa-miR-30b-5p.

33. The method according to claim 31, wherein the $\Delta Cq$ values are the values of the particular microRNA assays for hsa-miR-141-3p, hsa-miR-24-3p, and hsa-miR-31-5p, normalized with respect to the Cq values of the mean of the Cq values for microRNA assays for hsa-miR-200b-3p, hsa-miR-27b-3p, and hsa-miR-30b-5p.

34. A method of treating a patient in need of prostate cancer treatment, the method comprising: performing a diagnostic test according to claim 1 to determine if the patient has an increased probability of suffering from prostate cancer, and selecting an appropriate therapy for the patient based on this information.

* * * * *